United States Patent [19]

Vandenberk et al.

[11] 4,335,127

[45] Jun. 15, 1982

[54] PIPERIDINYLALKYL QUINAZOLINE COMPOUNDS, COMPOSITION AND METHOD OF USE

[75] Inventors: Jan Vandenberk, Beerse; Ludo Kennis, Vosselaar; Marcel Van der Aa; Albert Van Heertum, both of Vosselaar, all of Belgium

[73] Assignee: Janssen Pharmaceutica, N.V., Beerse, Belgium

[21] Appl. No.: 84,272

[22] Filed: Oct. 12, 1979

Related U.S. Application Data

[63] Continuation-in-part of Ser. No. 1,493, Jan. 8, 1979, abandoned.

[51] Int. Cl.$^3$ .................. C07D 401/06; A61K 31/445
[52] U.S. Cl. .................. 424/251; 544/284; 544/285; 544/286; 544/287; 542/424; 546/193; 546/194; 546/208; 546/212; 546/213; 546/225; 546/207

[58] Field of Search ............... 544/284, 285, 286, 287; 424/251

[56] References Cited

U.S. PATENT DOCUMENTS

| | | | |
|---|---|---|---|
| 3,322,766 | 5/1967 | Schipper | 544/284 |
| 3,635,976 | 1/1972 | Shetty | 544/284 |
| 4,096,144 | 6/1978 | Yamamoto et al. | 544/284 |
| 4,099,002 | 7/1978 | Inaba et al. | 544/284 |
| 4,146,717 | 3/1979 | Yamamoto et al. | 544/284 |

*Primary Examiner*—Anton H. Sutto
*Assistant Examiner*—James H. Turnipseed
*Attorney, Agent, or Firm*—Geoffrey G. Dellenbaugh

[57] ABSTRACT

Novel quinazoline derivatives, comprising in the heterocyclic part of their quinazoline nucleus at least one carbonyl or thiocarbonyl group and a particularly substituted piperidinyl-alkyl side chain, said compounds being potent serotonin-antagonists.

15 Claims, No Drawings

PIPERIDINYLALKYL QUINAZOLINE COMPOUNDS, COMPOSITION AND METHOD OF USE

CROSS-REFERENCE TO RELATED APPLICATIONS

This application is a continuation-in-part of our co-pending application Ser. No. 1,493, filed Jan. 8, 1979, now abandoned.

BACKGROUND OF THE INVENTION

There are known in the art a number of pharmacologically active quinazolinones which are substituted on their heterocyclic ring with a piperidinylalkyl side chain. Such compounds may be found in the following references:

U.S. Pat. Nos. 3,322,766; 3,528,982; 3,635,976; 3,812,257; 3,865,827; 4,096,144; and 4,099,002;

Fr. Pat. No. 1,431,815; and

J. Med. Chem., 8, 807 (1965).

The compounds of the present invention differ from the foregoing essentially by the presence of particular substituent groups on the piperidine ring of the piperidinyl-alkyl side chain.

In U.S. Pat. No. 4,035,369 there are described a series of 1-(benzazolylalkyl)-4-substituted piperidines, from which the subject compound of this invention differ essentially by the replacement of the benzazole group by a quinazoline group.

DESCRIPTION OF THE PREFERRED EMBODIMENTS

This invention is concerned with a novel series of quinazoline derivatives which are structurally represented by the formula

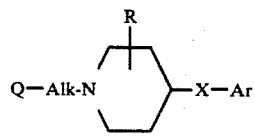

and the pharmaceutically acceptable acid addition salts thereof, wherein:

Ar is an aryl radical;

X is a member selected from the group consisting of

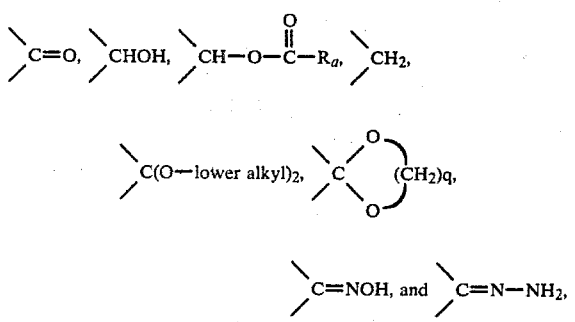

wherein said $R_a$ is hydrogen or lower alkyl and said q is the integer 2 or 3;

R is a member selected from the group consisting of hydrogen, hydroxy and lower alkyl;

Alk is an alkylene chain having from 1 to 4 carbon atoms; and

Q is a quinazolinyl radical, the 1-, 2-, 3- or 4-position of which is connected with the alkylene side chain, said quinazolinyl radical bearing in one or both of its 2- and 4-positions a carbonyl or thiocarbonyl group, wherein the benzene ring of said quinazolinyl radical is optionally substituted with 1 to 3 substituents each independently selected from the group consisting of halo, lower alkyl, lower alkyloxy, trifluoromethyl, nitro and cyano, and wherein the pyrimidino ring of said quinazolinyl radical may be partly or fully saturated, said pyrimidino ring being optionally substituted with 1 to 3 substituents independently selected from the group consisting of lower alkyl, aryl and aryl(lower alkyl);

wherein said aryl as used in the definition of said Ar and of said Q is a member selected from the group consisting of phenyl, substituted phenyl, thienyl and pyridinyl, wherein said substituted phenyl has from 1 to 3 substituents each independently selected from the group consisting of halo, lower alkyl, lower alkyloxy, trifluoromethyl and amino.

As used in the foregoing definitions the term "lower alkyl" is meant to include straight and branched hydrocarbon radicals having from 1 to 6 carbon atoms, such as, for example, methyl, ethyl, 1-methylethyl, 1,1-dimethylethyl, propyl, butyl, pentyl, hexyl and the like; "alkylene" as used in the definition of Alk comprises straight and branched alkylene chains having from 1 to 4 carbon atoms; and the term "halo" is generic to fluoro, chloro, bromo and iodo.

Examples of quinazolinyl radicals within the scope of Q are optionally substituted 1,4-dihydro-2,4-dioxo-3(2H)-quinazolinyl, 3,4-dihydro-2,4-dioxo-1(2H)-quinazolinyl, 3,4-dihydro-4-oxo-1(2H)-quinazolinyl, 1,2,3,4-tetrahydro-4-oxo-2-quinazolinyl, 1,4-dihydro-4-oxo-3(2H)-quinazolinyl and the like radicals.

Preferred compounds within the scope of formula (I) are those wherein X represents CO. Particularly preferred compounds are those wherein X is CO and Alk represents an 1,2-ethanediyl radical. The compound 3-[2-[4-(4-fluorobenzoyl)-1-piperidinyl]ethyl]-2,4-(1H,3H)-quinazolinedione is especially preferred.

The compounds of formula (I) have basic properties and, consequently, they may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, propanedioic, butanedioic, (Z)-2-butanedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) can generally be prepared by the reaction of an appropriate reactive ester of the formula (II), wherein Q and Alk are as previously defined and W is a reactive ester residue such as, for example, halo, particularly chloro, bromo or iodo, or a sulfonyloxy radical such as methylsulfonyloxy, 4-methylphenylsulfonyloxy and the like, with an appropriate piperidine derivative of the formula (III) wherein R, X and Ar have the previously defined meanings.

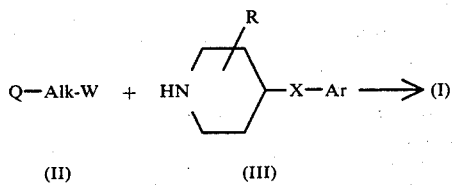

The foregoing reaction may be carried out following standard N-alkylating procedures. Said reaction is preferably carried out in an appropriate reaction-inert organic solvent such as, for example, a lower alkanol, e.g., methanol, ethanol, propanol, butanol and the like alkanols; an aromatic hydrocarbon, e.g., benzene, methylbenzene, dimethylbenzene, and the like; an ether, e.g., 1,4-dioxane, 1,1'-oxybispropane and the like; a ketone, e.g., 4-methyl-2-pentanone; N,N-dimethylformamide; nitrobenzene; and the like. The addition of an appropriate base such as, for example, an alkali or earth alkaline metal carbonate or hydrogen carbonate, may be utilized to pick up the acid which is liberated during the course of the reaction. A small amount of an appropriate metal iodide, e.g., sodium or potassium iodide may be added as a reaction promotor. Somewhat elevated temperatures are appropriate to enhance the rate of the reaction and preferably the reaction is carried out at the reflux temperature of the reaction mixture.

The compounds of formula (I) may also be prepared starting from a corresponding intermediate of the formula (IV)

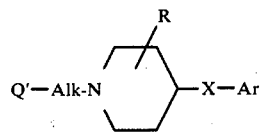

wherein Alk, R, X and Ar are as previously defined and Q' is an appropriate precursor of Q, by converting said Q' into said Q following art-known procedures. Such procedures are described, for example, in "The Chemistry of Heterocyclic Compounds-Fused Pyrimidines; Part I: Quinazolines", Ed. D. J. Brown, Interscience Publishers; New York, London, Sidney (1967), p. 74–102 and p. 116–128. Examples of such conversions of Q' into Q are given hereafter.

In order to simplify the structural representation of the compounds of formula (I) and of certain precursors and intermediates thereof the appropriately substituted piperidinylalkyl radical of the formula

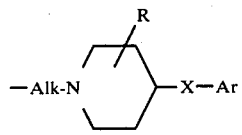

will hereinafter be represented by the symbol D.

The compounds of formula (I) wherein Q represents a 1,2,3,4-tetrahydro-4-oxo- or 4-thioxo-quinazolinyl radical, said compounds being represented by the formula (I-a), can be prepared by cyclizing an appropriately substituted 2-aminobenzamide or -benzenethioamide of formula (IV-a) with an appropriately substituted carbonyl or thiocarbonyl compound of formula (V). In the following reaction-equation one of $R^2$, $R^3$, $R^4$ and $R^5$ is D, each of the remaining being independently selected from the group consisting of hydrogen, lower alkyl, aryl and aryllower alkyl; $R^1$ is selected from the group consisting of halo, lower alkyl, lower alkyloxy, trifluoromethyl, nitro and cyano; each Y is O or S; and n is an integer of from 0 to 3 inclusive.

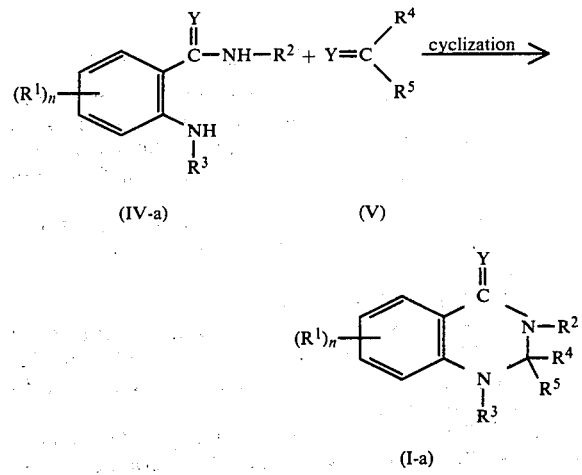

Said cyclization-reaction may conveniently be carried out by stirring the reactants together in the presence of an appropriate solvent such as, for example, a lower alkanol, e.g., methanol, ethanol, propanol and the like. Somewhat elevated temperature and the addition of a catalytic amount of an appropriate strong acid, e.g., 4-methylbenzenesulfonic acid, hydrochloric acid and the like, may be used to enhance the rate of the reaction. Most preferably the reaction is carried out at the reflux temperature of the reaction mixture. In the foregoing reaction the reagent of formula (V) may be replaced by an appropriate functionally equivalent derivative thereof such as, for example, a di(lower alkyl)actal, a cyclic acetal and the like.

The compounds of formula (I) wherein Q represents a 3,4-dihydro-4-oxo-2-quinazolinyl radical, a 4-oxo-3(4H)-quinazolinyl radical or a corresponding thioxo analog thereof, said compounds being represented by the formula (I-b), can be derived from an appropriately substituted 2-aminobenzamide or -benzenethioamide of formula (IV-a) wherein $R^3$ is hydrogen, (IV-a-1), by converting (IV-a-1) into the corresponding 2-(acylamino)benzamide or -benzenethioamide of formula (VI) and cyclizing the latter following art-known cyclizing procedures. In the following reaction-equations either of $R^2$ and $R^4$ is D, the other being a member selected from the group consisting of hydrogen, lower alkyl, aryl and aryllower alkyl.

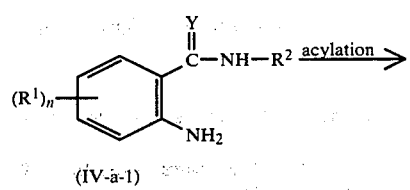

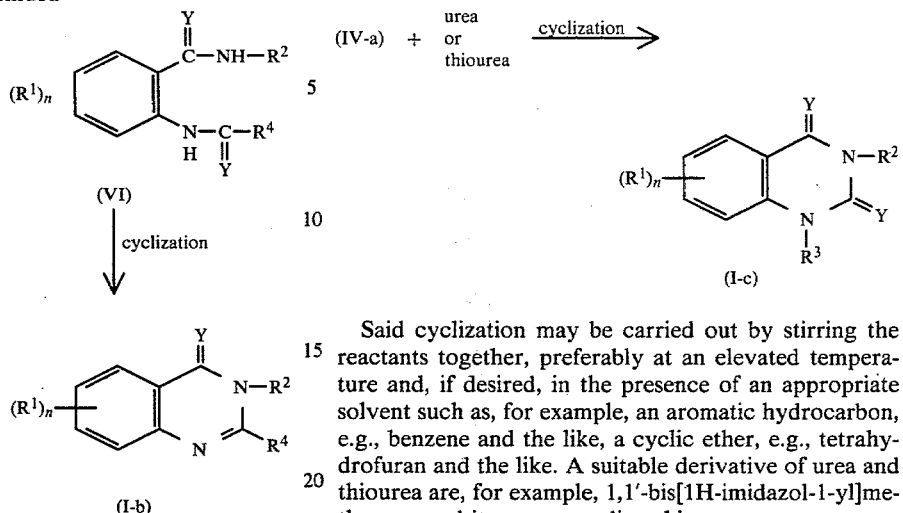

(VI)

↓ cyclization

(I-b)

The foregoing cyclization reaction may be carried out by stirring and heating, preferably refluxing, the 2-(acylamino)benzamide or -benzenethioamide (VI) in a suitable reaction-inert solvent such as, for example, a lower alkanol, e.g., methanol, ethanol, 2-propanol and the like; an aliphatic or aromatic hydrocarbon, e.g., hexane, benzene, methylbenzene and the like; a halogenated hydrocarbon, e.g., trichloromethane and the like. In order to enhance the rate of the reaction there may be added an appropriate base such as, for example, an alkali or earth alkaline earth hydroxide, carbonate or hydrogencarbonate, e.g., sodium hydroxide, potassium carbonate, sodium hydrogen carbonate and the like. The conversion of the 2-aminobenzamide or -benzenethioamide (IV-a-1) into the 2-(acylamino)benzamide or -benzenethioamide (VI) may be carried out by reacting (IV-a-1) with an appropriate acylating agent derived from the acid $$\underset{\text{R}^4-\overset{\overset{Y}{\|}}{C}-OH}{} \qquad (VII)$$

wherein $R^4$ has the previously defined meaning. Appropriate acylating agents include anhydride and acyl halides derived from (VII). The acid (VII) itself may optionally be used as an acylating agent. In the latter case it is appropriate to remove the water formed during the course of the reaction by azeotropic distillation.

The compounds of formula (I) wherein Q is a 1,4-dihydro-2,4-dioxo-3(2H)-quinazolinyl radical, a 3,4-dihydro-2,4-dioxo-1(2H)-quinazolinyl radical or a mono- or dithioxo derivative thereof, said compounds being represented by the formula (I-c), may be derived from an appropriate 2-aminobenzamide or -benzenethioamide of formula (IV-a), by cyclizing the latter with urea, thiourea or a functionally equivalent derivative thereof. In the following reaction scheme one of $R^2$ and $R^3$ is D, the remaining being selected from the group consisting of hydrogen, lower alkyl, aryl and aryllower alkyl, $R^1$ and n are as previously described and each Y is independently selected from the group consisting of O and S.

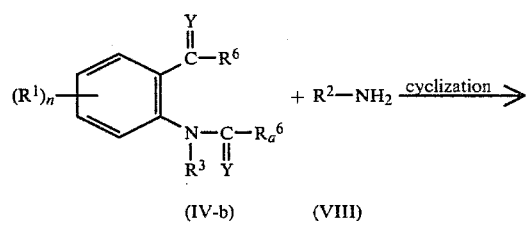

Said cyclization may be carried out by stirring the reactants together, preferably at an elevated temperature and, if desired, in the presence of an appropriate solvent such as, for example, an aromatic hydrocarbon, e.g., benzene and the like, a cyclic ether, e.g., tetrahydrofuran and the like. A suitable derivative of urea and thiourea are, for example, 1,1'-bis[1H-imidazol-1-yl]methanone and its corresponding thione.

The compounds of formula (I-c) may also be prepared by cyclizing an appropriately substituted compound of formula (IV-b) with an appropriate primary amine of the formula (VIII). In the following reaction-scheme, Y, $R^1$ and n have the previously defined meanings, one of $R^2$ and $R^3$ is D, the other hydrogen, lower alkyl or aryllower alkyl and $R^6$ and $R^6_a$ each represent an appropriate leaving group such as, for example, lower alkyloxy, amino and mono- and di(lower alkyl)amino.

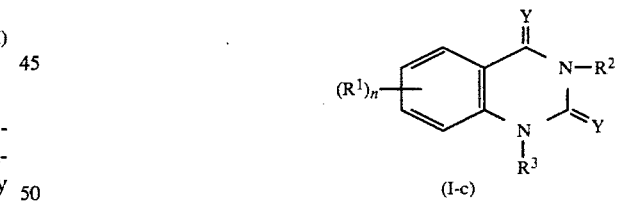

The compounds of formula (I-c) wherein $R^3$ is hydrogen and $R^2$ is D, said compounds being represented by the formula (I-c-1), can also be prepared by cyclizing an isocyanate or an isothiocyanate of formula (IV-c) with a primary amine of formula (VIII) wherein $R^2$ is D, (VIII-a). In the following reaction-equation $R^6$ represents an appropriate leaving group and $R^1$, n and Y are as previously described.

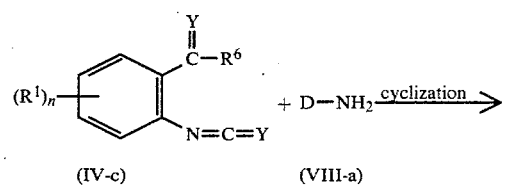

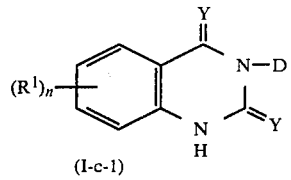

(I-c-1)

The compounds of formula (I-c) wherein $R^3$ is D and $R^2$ is hydrogen, said compounds being represented by the formula (I-c-2), can also be prepared by cyclizing an appropriately substituted benzenamine or benzenethioamine of formula (IV-d), wherein D, Y and $R^6$ are as previously described, with an alkali metal cyanate or thiocyanate, e.g., potassium cyanate, sodium thiocyanate and the like.

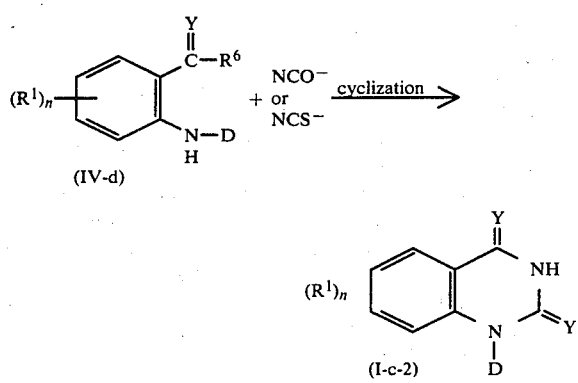

(IV-d)

(I-c-2)

Said cyclization-reactions are conveniently carried out by stirring and heating the reactants together, optionally in a suitable reaction-inert solvent having a relatively high boiling point such as aliphatic and aromatic hydrocarbons, e.g., petroleum ether, dimethylbenzene and the like.

The compounds of formula (I) wherein Q is a 1,4-dihydro-2-oxo-3(2H)-quinazolinyl radical and wherein X is as previously described but other than >CO, said X being represented by X' and said compounds being represented by the formula (I-d), may also be prepared by acylating an intermediate of formula (IV-e) wherein $R^7$ is hydrogen, lower alkyl, aryl or aryllower alkyl and $R^1$, n and $R^3$ are as previously described, with a trihalo-acetic or -ethanethioic acid, or an acid halide thereof, subsequently reacting the thus obtained acylate (IX) with an amine of formula (VIII-b) and cyclizing the thus obtained Schiff's base (X) in the presence of an appropriate reducing aget, e.g., sodium borohydride and the like.

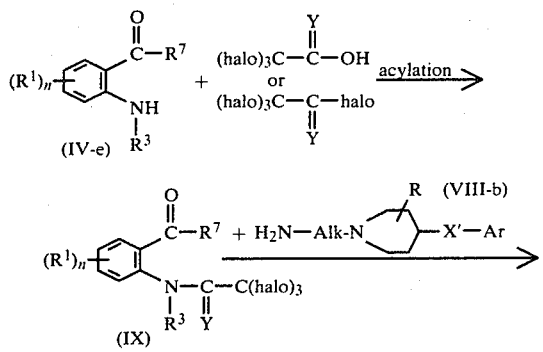

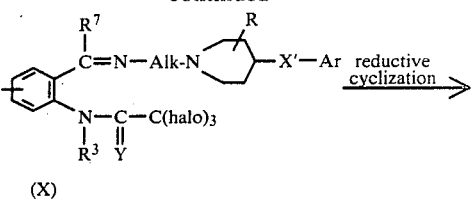

(X)

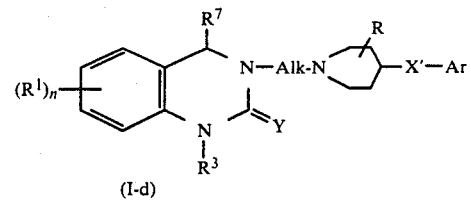

(I-d)

The acylation is carried out following art-known acylating procedures. The Schiff's base is prepared by stirring and heating the intermediates (IX) and (VIII-b) together in the presence of a suitable solvent, such as, for example, an alcohol, e.g., methanol and the like. The reductive cyclization is carried out by stirring the Schiff's base (X) and the reducing agent, e.g., sodium borohydride and the like, together in the presence of a suitable solvent, e.g., N,N-dimethylformamide and the like. Sometimes external cooling may be appropriate.

The compounds of formula (I) may also be derived from a compound of formula (XI) wherein P represents a precursor of the corresponding Ar-X-radical by converting said P into the desired Ar-X following methods known in the art.

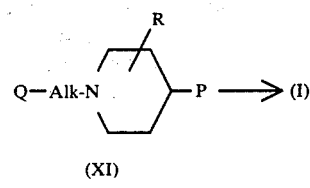

(XI)

For example, the compounds of formula (I) wherein Ar-X-is an optionally substituted 2-aminobenzoyl radical, said compounds being represented by the formula (I-e), may be prepared by the oxidative cleavage of the double bond in the corresponding indole-derivative (XII) and subsequent hydrolysis of the thus formed formamide (XIII). Said oxidative cleavage may be carried out by the reaction of (XII) with an appropriate oxidizing agent, such as, for example, sodium periodate in the presence of a catalytic amount of osmiumtetroxide in a suitable solvent, e.g. 1,4-dioxane and the like. The oxidation may equally well be carried out by bubbling ozonized oxygen through a solution of (XII) in acetic acid and subsequently decomposing the intermediately formed ozonide with water. The thus obtained (formylamino)phenylcarbonyl intermediate (XIII) is then converted into (I-e) by hydrolysis in acidic medium. In the following reaction-equations $R^8$ and $R^9$ are each independently selected from the group consisting of hydrogen, halo, lower alkyl, lower alkyloxy, trifluoromethyl and amino.

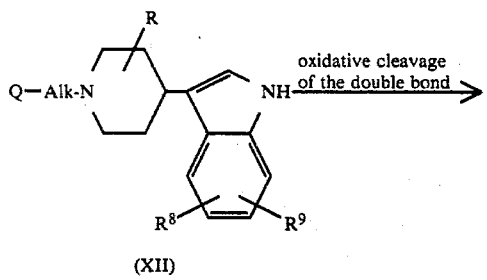

(XII)

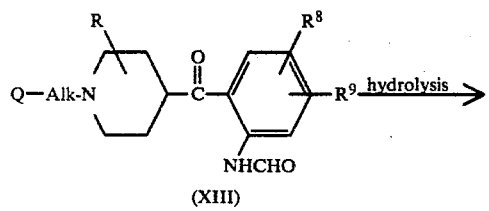

(XIII)

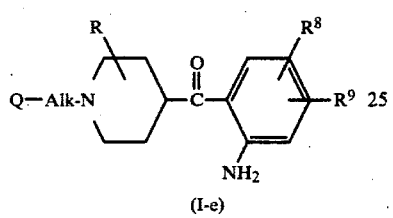

(I-e)

The compounds of formula (I) wherein X is a CHOH radical, (I-f), may generally be prepared starting from the corresponding carbonyl-derivatives, (I-g), by reducing the carbonyl group of the latter with an appropriate reducing agent, e.g. sodium borohydride, sodium cyanoborohydride and the like following art-known methodologies.

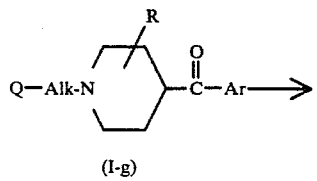

(I-g)

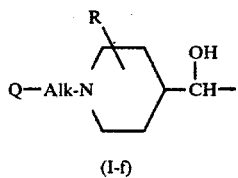

(I-f)

When, for example, sodium borohydride is used as a reducing agent the reaction may conveniently be carried out in alkaline aqueous medium, if desired, in admixture with a water-miscible organic solvent such as, for example, an alicyclic ether, e.g. tetrahydrofuran, 1,4-dioxane and the like; or a lower alkanol, e.g. methanol, propanol and the like.

The compounds of formula (I) wherein X represent a radical >CHOC(O)-$R_a$, wherein $R_a$ has the previously defined meaning, said compounds being represented by the formula (I-h), may be derived from the corresponding alcohols (I-f) by acylating the latter with an appropriate acylating agent according to art-known procedures. Appropriate acylating agents which may be used for this purpose include lower alkanoic acids and acyl halides and anhydrides derived therefrom.

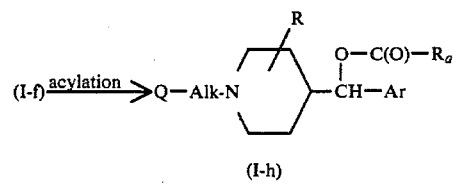

(I-h)

The compounds of formula (I) wherein X is a methylene radical, (I-j), may be derived from the corresponding carbonyl derivatives (I-g) by the reduction of the carbonyl group of (I-g) to a methylene group, e.g. by the Clemmensen reduction, using amalgated zinc and hydrochloric acid, or by the Wolff-Kishner reduction, using hydrazine and alkali in a high-boiling polar solvent, such as, 1,2-ethanediol and the like.

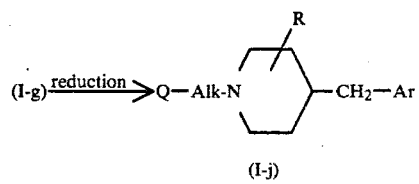

(I-j)

The compounds of formula (I) wherein X represents a di(lower alkyl)ketal or a cyclic lower alkylene ketal, wherein the lower alkylene chain has from 2 to 4 carbon atoms, may be derived from the corresponding carbonyl compounds by subjecting the latter to a ketalization-reaction following methodologies generally known in the art. Cyclic lower alkylene ketals, for example, may be prepared following methodologies analogous to those described in Synthesis, 1974, (I) 23-26.

The compounds of formula (I) wherein X represents a radical of the formula >C=NOH or a radical of the formula >C=N-$NH_2$ can easily be derived from the corresponding carbonyl compounds by reacting the latter with respectively hydroxylamine hydrochloride or hydrazine hydrochloride according art-known procedures of preparing oximes and hydrazones.

Certain of the intermediates and starting materials used in the foregoing preparations are known compounds, others may be prepared according to art-known methodologies of preparing similar compounds and some of them are novel and consequently their preparation will be described hereafter.

The intermediates of formula (II) can be prepared by converting the hydroxyl function of the corresponding alcohol (XIV) into a reactive leaving group, e.g., by reacting the alcohol (XIV) with thionyl chloride, sulfuryl chloride, phosphor pentabromide, phosphoryl chloride, methanesulfonyl chloride, 4-methylbenzenesulfonyl chloride and the like. The alcohols (XIV), used as starting materials herein, can be derived from an alcohol (XV) wherein Q' is a precursor of Q following similar procedures as previously described herein for the preparation of (I-a), (I-b), (I-c) and (I-d) starting from appropriate intermediates of formula (IV).

Alternatively, the intermediates of formula (II) can be derived from an alcohol (XV) by converting the hydroxyl function into a reactive leaving group and subsequently cyclizing the precursor Q' in the thus obtained intermediate (XVI) following the previously described procedures. In the following reaction-scheme Q, Q', Alk and W have the previously defined meanings.

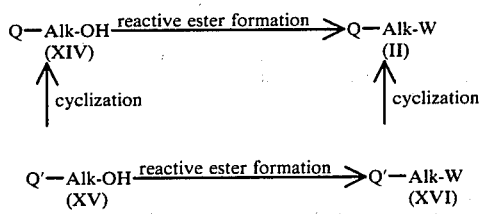

The intermediates of the formula (III) may be derived from an intermediate of formula (XVII) by eliminating the protective group Z following art-known procedures.

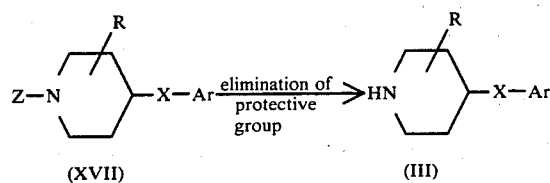

Said elimination of Z can be carried out following art-known procedures, depending upon the nature of Z, e.g., by catalytically hydrogenating a benzyl analog of (XVII), in case Z is benzyl, or by hydrolyzing a lower alkyloxycarbonyl analog of formula (XVII) in acidic medium, in case Z is lower alkyloxycarbonyl.

The intermediates of formula (XVII) may be prepared following art-known procedures. For example, the intermediates of formula (XVII) wheren X is CO, (XVII-a), may be prepared starting from an appropriately substituted 4-piperidinone (XVIII) and an appropriate arylmethylcyanide (XIX) as shown in the following reaction-scheme.

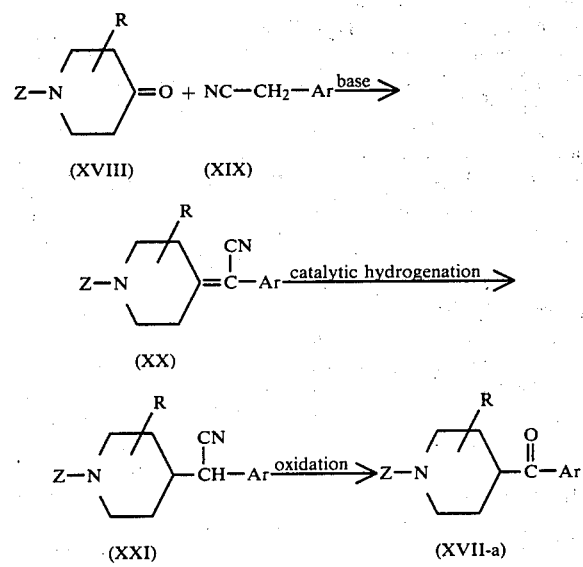

The reaction of (XVIII) and (XIX) can be carried out by stirring and, if desired, heating the reactants together in a suitable reaction-inert solvent and in the presence of an appropriate base such as, for example, an alkali metal alkanolate, e.g., sodium methanolate and the like. The catalytic hydrogenation of (XX) is desirably conducted in a suitable reaction-inert solvent such as, for example, a lower alkanol, e.g., methanol and the like, in the presence of an appropriate catalyst, e.g., palladium-on-charcoal and the like. In order to avoid hydrogenation of the nitrile group it may be appropriate to add an appropriate catalyst-poison, e.g., thiophene and the like. The oxidation of the thus obtained (XXI) can be carried out following art-known oxidative procedures, e.g., as described in Journal of Organic Chemistry 40, 267 (1975).

The intermediates of formula (XVII-a), wherein R is other than hydroxy, said R being represented by R' and said intermediates by (XVII-a-1), can also be prepared by the Grignard reaction of an appropriately substituted 4-piperidinyl magnesium halide (XXII) with an appropriate aryl cyanide (XXIII).

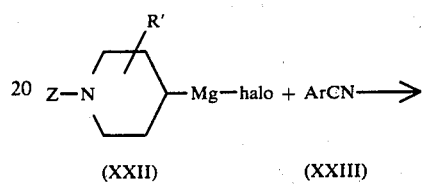

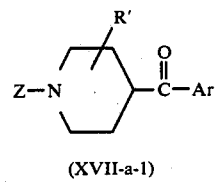

Said Grignard-reaction is carried out by stirring and, if desired, heating the reactants together in the presence of a suitable reaction-inert solvent, e.g., 1,1'-oxybisethane, tetrahydrofuran and the like.

The intermediates of formula (III) wherein X is other than CO, (III-b), can be derived from the corresponding arylcarbonylpiperidines, (III-a), following the same procedures as described hereinbefore for the preparation of compounds (I) wherein X is other than >C=O, starting from (I-g).

The intermediates of formula (IV) can generally be prepared by N-alkylating a piperidine (III) with an appropriately substituted reactive ester (XVI) following art-known N-alkylating procedures, as previously described herein for the preparation of compounds (I) starting from (II) and (III).

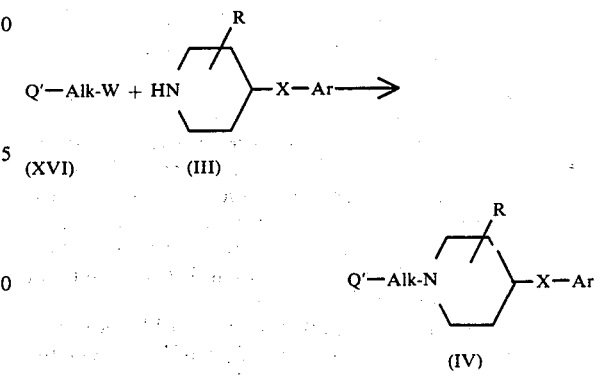

The intermediates of formula (IV-a-1) can also be prepared by reducing the corresponding nitro-derivatives (XXIV) following art-known nitro-to-amine reduction reactions as known in the art, e.g., by catalytically hydrogenating the nitro-derivatives (XXIV) in the presence of an appropriate catalyst, e.g., platinum-on-charcoal and the like, in the presence of a suitable reaction-inert solvent, e.g., a lower alkanol such as methanol and the like. A catalyst poison, e.g., thiophene and the like may be appropriate to avoid undesired reductions of other functional groups.

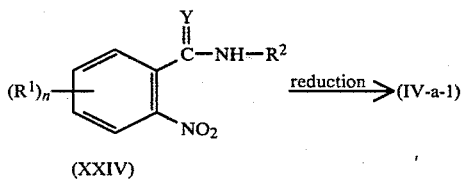

(XXIV)

The intermediates of formula (IV-a) can generally be derived from the intermediates (IV-a-1) by N-alkylating the latter with an appropriate reactive ester R³-W, (XXV), following art-known N-alkylating procedures.

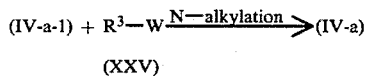

The nitro-derivatives (XXIV) may themselves be prepared by N-alkylating an appropriately substituted 2-nitrobenzamide (XXVI) with an appropriate compound of the formula (XXVII) wherein W and W' are each a reactive leaving group, provided that W' has better leaving capacity than W. The thus obtained (XXVIII) is subsequently reacted with an appropriately substituted piperidine derivative (III).

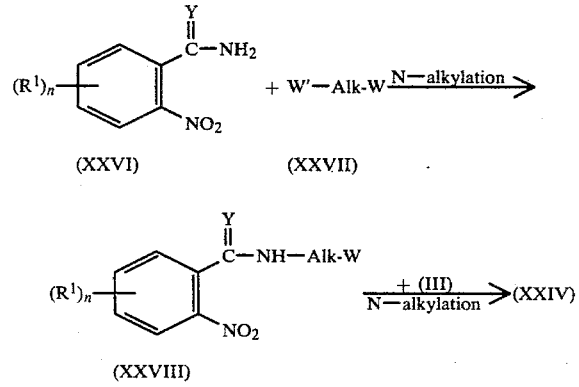

Both N-alkylations are carried out following art-known procedures as previously described herein for the preparation of compounds (I) starting from (II) and (III).

The intermediates of formula (XII) may be prepared by N-alkylating a piperidine (XXIX), wherein R, R⁸ and R⁹ are as previously defined, with an appropriate reactive ester of the formula (II) following standard N-alkylating procedures.

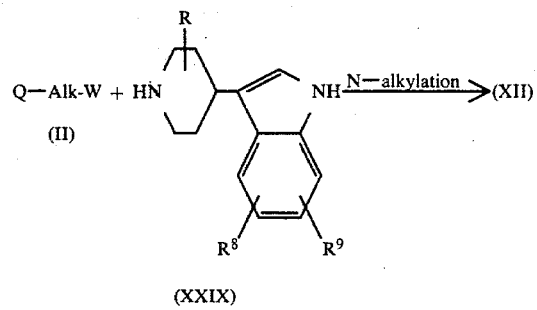

(XXIX)

The starting compounds (XXIX) herein are described in Belg. Pat. No. 858,101 and can be prepared by condensating benzoyl chloride with an appropriately substituted pyridine (XXX) and an appropriately substituted 1H-indole (XXXI), subsequently reducing the thus obtained dihydro-pyridine (XXXII), e.g., by catalytically hydrogenating the latter in the presence of an appropriate catalyst, such as, for example, palladium-on-charcoal and the like, and hydrolyzing the benzoyl derivative (XXXIII) in alkaline medium.

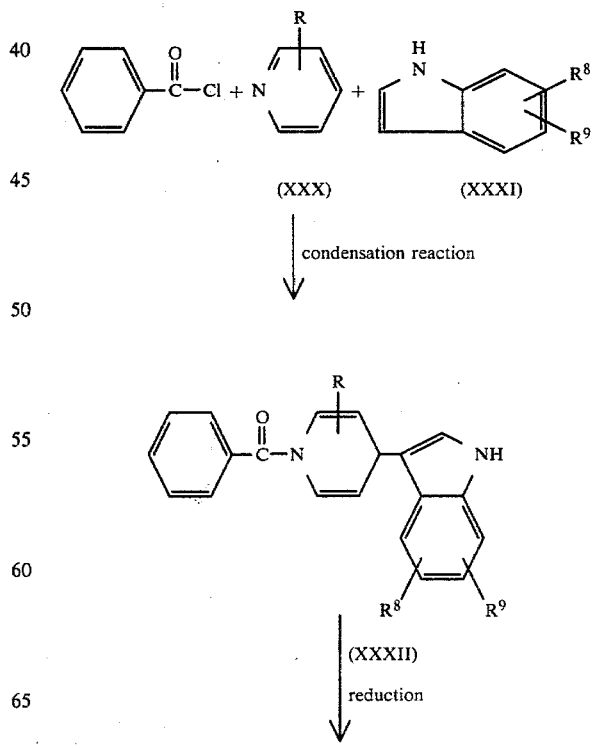

-continued

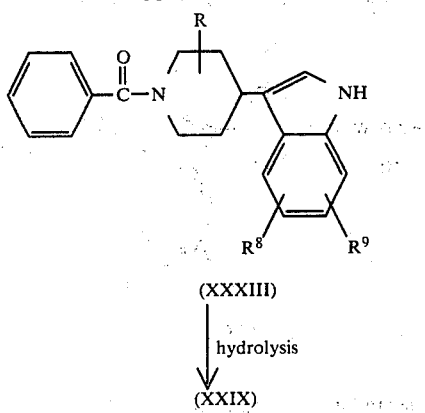

(XXXIII)

↓ hydrolysis (XXIX)

The compounds of formula (I), the intermediates of formula (XII) and their pharmaceutically active acid addition salts have useful pharmacological properties. They are very potent serotonin-antagonists and as such they can be used in the treatment of a variety of diseases in which serotonin release is of predominant importance.

The potency of the subject compounds as serotonin-antagonists is clearly evidenced by the results obtained in the following tests wherein the antagonistic activity of the compounds (I) on the effect of serotonin is examined.

Test 1: Antagonistic Activity on the Effect of Serotonin on the Caudal Artery of the Rat Caudal arteries from fasted male rats (210-235 g) are used in the test. Two helical strips having a length of 5-6 cm and a width of 2 mm are obtained from each artery and mounted vertically in a 100 ml organ bath containing an oxygenated Krebs-Henseleit solution. Submaximal contractions of the arterial strips are produced by adding single doses of serotonin (40 ng/ml) to the organ bath for 2 minutes with each time an interval of 10 minutes. The amplitude of the contraction is measured before and 5 minutes after adding the drug. After washing out, the agonist is added again three times in order to see whether the contraction is restored and normalized. The first column of table 1 shows the $ED_{50}$-values in ng/ml for a number of compounds of formula (I) in the above test. In this connection the $ED_{50}$-values are the minimal concentrations of the concerned drugs which reduce the amplitude of the contraction to at least 50% of its normal value.

Test 2: Effects in Gastric Lesion Tests

A. Lesions Induced by Compound 48/80

Compound 48/80 (a mixture of oligomers obtained by condensation of 4-methoxy-N-methylbenzenethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1 antagonist. However the stimulatory effects on gastric secretion are not suppressed so that rats treated with compound 48/80 and protected from shock by an H 1 antagonist may exhibit all signs of intensive gastric gland activity: gross autopsy shows distended stomachs with abnormal contents and rough bright red patches all over the mucosa, corresponding to areas of disintegrated glands. A number of known serotonin antagonists such as, for example, methysergide, cyproheptadine, cinanserin, mianserin, pipamperone, spiperone, pizotifen and metergoline, prevent completely the cyanosis of ears and extremities as well as the lesions in the glandular area of the stomach and the abnormal gastric distension.

B. Method

Male rats of a Wistar inbred strain, weighing 220-250 g, are starved overnight, water being available ad libitum. The test compounds are administered orally as a solution or as a suspension in aqueous medium. A control rat and a "blank" rat receive the test compound. One hour later 5-[4-(diphenylmethyl)-1-piperazinylmethyl]-1-methyl-1H-benzimidazole-2-methanol is administered subcutaneously to all rats at the dose of 2.5 mg/kg. Two hours after the oral administration of the test compound the compound 48/80 (freshly solved in water at a concentration of 0.25 mg/ml) is injected intravenously into all rats (dose: 1 mg/kg) except the "blank" rats. Five minutes after the injection the intensity of purple-blue coloration (cyanosis) of the extremities is scored as 0 (absent), +(moderate) or ++(intense). Four hours after the intravenous injection of compound 48/80 the rats are decapitated and the stomachs are removed. Subsequently the stomachs are inspected for distension and contents (blood, fluid, food) and thoroughly rinsed. The macroscopic lesions are scored from 0 to +++, 0 corresponding to complete absence of visible lesions and the highest score corresponding to reddish rough patches covering more than half the glandular area.

The second column of table 1 shows for a number of compounds of formula (I) the doses (in mg/kg body weight) at which the distension of the stomach as well as the lesions in the glandular area of the stomach are completely absent in 50% of the test rats ($ED_{50}$-values).

The third column of table 1 shows for a number of compounds of formula (I) the doses (in mg/kg body weight) at which the cyanosis of ears and extremities is completely absent in 50% of the test rats ($ED_{50}$-values).

The compounds listed in table 1 are not given for the purpose of limiting the invention thereto but only to exemplify the useful pharmacological activities of all the compounds within the scope of formula (I).

TABLE 1

| $(R^1)_n$ | $R^3$ | Y | Alk | R | X | Ar | Caudal artery ng/ml | G. lesion ED$_{50}$ in mg/kg | Cyanosis ED$_{50}$ in mg/kg |
|---|---|---|---|---|---|---|---|---|---|
| — | H | O | —(CH$_2$)$_3$— | — | —CO— | 4-F—C$_6$H$_4$ | 1.25 | 2.5 | — |
| — | H | O | —(CH$_2$)$_2$— | — | —CO— | 4-F—C$_6$H$_4$ | 0.7 | 0.16 | 0.08 |
| — | H | O | —(CH$_2$)$_2$— | — | —CO— | 4-Cl—C$_6$H$_4$ | 2.5 | — | — |
| — | H | O | —(CH$_2$)$_2$— | — | —CO— | 4-OCH$_3$—C$_6$H$_4$ | 2.5 | — | — |
| — | H | S | —(CH$_2$)$_3$— | — | —CO— | 4-F—C$_6$H$_4$ | 2 | 2.5 | 0.63 |
| — | H | S | —(CH$_2$)$_2$— | — | —CO— | 4-F—C$_6$H$_4$ | 0.6 | 0.08 | 0.04 |
| 7-Cl | H | O | —(CH$_2$)$_2$— | — | —CO— | 4-F—C$_6$H$_4$ | 2 | 1.25 | 1.25 |
| — | CH$_3$ | O | —(CH$_2$)$_2$— | — | —CO— | 4-F—C$_6$H$_4$ | 0.7 | 1.25 | 0.16 |
| — | H | O | —(CH$_2$)$_2$— | — | —CO— | 2-NH$_2$, 4-F—C$_6$H$_3$ | 0.6 | 1.25 | 0.16 |
| 7-F | H | O | —(CH$_2$)$_2$— | — | —CO— | 4-F—C$_6$H$_4$ | 0.7 | 1.25 | 0.16 |
| 7-OCH$_3$ | H | O | —(CH$_2$)$_2$— | — | —CO— | 4-F—C$_6$H$_4$ | 0.7 | 0.31 | 0.16 |
| 6-CH$_3$ | H | O | —(CH$_2$)$_2$— | — | —CO— | 4-F—C$_6$H$_4$ | 1.3 | 2.5 | 0.63 |
| — | H | O | —(CH$_2$)$_2$— | — | —CHOH— | 4-F—C$_6$H$_4$ | 20 | 1.25 | 1.25 |
| — | H | O | —(CH$_2$)$_2$— | — | >C<(O—)(O—) (dioxolane) | 4-F—C$_6$H$_4$ | 11 | 0.31 | 0.16 |

| $(R^1)_n$ | $R^4$ | Y | Alk | R | X | Ar | Caudal artery ng/ml | G. lesion ED$_{50}$ in mg/kg | Cyanosis ED$_{50}$ in mg/kg |
|---|---|---|---|---|---|---|---|---|---|
| — | H | O | —(CH$_2$)$_2$— | — | —CO— | 4-F—C$_6$H$_4$ | 0.6 | 0.31 | 0.31 |
| — | H | O | —(CH$_2$)$_3$— | — | —CO— | 4-F—C$_6$H$_4$ | 5 | 2.5 | — |
| — | CH$_3$ | O | —(CH$_2$)$_2$— | — | —CO— | 4-F—C$_6$H$_4$ | 0.6 | 0.16 | 0.16 |

| $(R^1)_n$ | $R^2$ | $R^3$ | $R^4$ | Alk | X | Ar | Caudal artery ng/ml | G. lesion ED$_{50}$ in mg/kg | Cyanosis ED$_{50}$ in mg/kg |
|---|---|---|---|---|---|---|---|---|---|
| — | H | H | H | —(CH$_2$)$_2$ | CO | 4-F—C$_6$H$_4$ | 0.7 | 2.5 | 1.25 |

| $(R^1)_n$ | $R^3$ | $R^4$ | $R^5$ | Alk | Ar | Caudal artery ng/ml | G. lesion ED$_{50}$ in mg/kg | Cyanosis ED$_{50}$ in mg/kg |
|---|---|---|---|---|---|---|---|---|
| — | H | H | H | —(CH$_2$)$_2$— | 4-F—C$_6$H$_4$ | 5 | ≧2.5 | — |
| — | H | H | H | —(CH$_2$)$_3$— | 4-F—C$_6$H$_4$ | 10 | ≧2.5 | — |

| $(R^1)_n$ | $R^6$ | Alk | Ar | Caudal artery ng/ml | G. lesion ED$_{50}$ in mg/kg | Cyanosis ED$_{50}$ in mg/kg |
|---|---|---|---|---|---|---|
| — | C$_6$H$_5$ | (CH$_2$)$_2$ | 4-F—C$_6$H$_4$ | 0.6 | 0.08 | 0.08 |
| 6-Cl | C$_6$H$_5$ | (CH$_2$)$_2$ | 4-F—C$_6$H$_4$ | — | 0.63 | 0.63 |

TABLE 1-continued

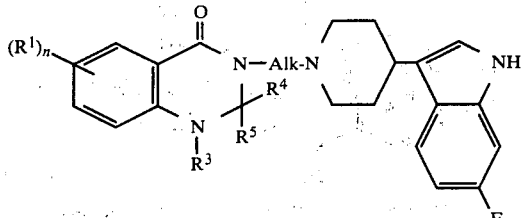

| $(R^1)_n$ | $R^3$ | $R^4$ | $R^5$ | Alk | Caudal artery ng/ml | G. lesion $ED_{50}$ in mg/kg | Cyanosis $ED_{50}$ in mg/kg |
|---|---|---|---|---|---|---|---|
| — | H | H | H | $(CH_2)_2$ | 0.7 | 0.31 | 0.16 |

The compounds of formula (I) and the intermediates of formula (XII) prevent completely the lesions which are caused by excessive serotonin release and they also block the serotonin-induced contractions of bronchial tissues and of blood vessels, arteries as well as veins, and, consequently, the compounds of the present invention can be used in the treatment of gastrointestinal ulcus, bronchial spasm, hemorrhoids, varises and the like diseases, all of which are caused by congestion.

In view of their useful anti-congestive properties, the subject compounds may be formulated into various pharmaceutical forms for administration purposes. To prepare the pharmaceutical compositions of this invention, an effective anti-congestive amount of the particular compound, in base of acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Although the amount of the active ingredient to be administered may vary within rather wide limits depending on the particular circumstances, such as the nature and the severity of the disease, doses of from about 0.04 to about 4 mg of active ingredient per kg of body weight, and particularly from about 0.1 to about 2 mg per kg of body weight, administered once or repeatedly, are in general satisfactory.

The following formulations exemplify typical anticonvulsant pharmaceutical compositions in dosage unit form suitable for systemic administration to animal and human subjects in accordance with the present invention. These examples are given to illustrate and not to limit the scope of the present invention.

Oral Drops

The following formulation provides 50 liters of an oral-drop solution comprising 10 mg of 3-[2-[4-(4-fluorobenzoyl)-1-piperidinyl]ethyl]-2,4(1H,3H)-quinazolinedione as the active ingredient (A.I.) per milliliter.

| A.I. | 500 | grams |
|---|---|---|
| 2-hydroxypropanoic acid | 0.5 | liters |
| sodium saccharin | 1750 | grams |
| cocoa flavor | 2.5 | liters |
| purified water | 2.5 | liters |
| polyethylene glycol q.s. ad | 50 | liters |

The A.I. is dissolved in the 2-hydroxypropanoic acid and 1.5 liters of the polyethylene glycol at 60°–80° C. After cooling to 30°–40° C. there are added 35 liters of polyethylene glycol and the mixture is stirred well. Then there is added a solution of the sodium saccharin in 2.5 liters of purified water and while stirring there are added the cocoa flavor and polyethylene glycol q.s. ad volume. The resulting solution is filled into suitable containers.

Oral Solution

The following formulation provides 20 liters of an oral solution comprising 20 mg of 3-[2-[4-(4-fluorobenzoyl)-1-piperidinyl]ethyl]-2,4(1H,3H)-quinazolinedione as the active ingredient (A.I.) per teaspoonful (5 milliliters).

| A.I. | 20 grams |
|---|---|
| 2,3-dihydroxybutanedioic acid | 10 grams |

|  |  |  |
| --- | --- | --- |
| sodium saccharin | 40 | grams |
| 1,2,3-propanetriol | 12 | liters |
| Sorbitol 70% solution | 3 | liters |
| Methyl 4-hydroxybenzoate | 9 | grams |
| Propyl 4-hydroxybenzoate | 1 | gram |
| Raspberry essence | 2 | milliliters |
| Gooseberry essence | 2 | milliliters |
| Purified water q.s. ad 20 liters. | | |

The methyl and propyl 4-hydroxybenzoates are dissolved in 4 liters of boiling purified water. In 3 liters of this solution are dissolved first the 2,3-dihydroxybutanedioic acid and thereafter the A.I.. The latter solution is combined with the remaining part of the former solution and the 1,2,3-propanetriol and the sorbitol solution are added thereto. The sodium saccharin is dissolved in 0.5 liters of water and the raspberry and gooseberry essences are added. The latter solution is combined with the former, water is added q.s. ad volume and the resulting solution is filled in suitable containers.

Capsules

The following formulation provides 1000 capsules comprising each 20 mg of 3-[2-[4-(4-fluorobenzoyl)-1-piperidinyl]ethyl]-2,4-(1H,3H)-quinazolinedione as the active ingredient (A.I.).

|  |  |  |
| --- | --- | --- |
| A.I. | 20 | grams |
| Sodium lauryl sulfate | 6 | grams |
| Starch | 56 | grams |
| Lactose | 56 | grams |
| Colloidal silicon dioxide | 0.8 | grams |
| Magnesium stearate | 1.2 | grams |

The composition is prepared by stirring the ingredients vigorously together. The resulting mixture is subsequently filled into suitable hardened gelatine capsules.

Film-coated Tablets 10.000 compressed tablets, each containing as the active ingredient 10 mg of 3-[2-[4-(4-fluorobenzoyl)-1-piperidinyl]ethyl]-2,4(1H,3H)-quinazolinedione, are prepared from the following formulation:

|  |  |  |
| --- | --- | --- |
| Tablet core: | | |
| A.I. | 100 | grams |
| Lactose | 570 | grams |
| Starch | 200 | grams |
| Polyvinylpyrrolidone (Kollidon-K 90) | 10 | grams |
| Microcrystalline cellulose (Avicel) | 100 | grams |
| Sodium dodecyl sulfate | 5 | grams |
| Hydrogenated vegetable oil (Sterotex) | 15 | grams |
| Coating: | | |
| Methyl cellulose (Methocel 60 HG) | 10 | grams |
| Ethyl cellulose (Ethocel 22 cps) | 5 | grams |
| 1,2,3-propanetriol | 2.5 | milliliters |
| Polyethylene glycol 6000 | 10 | grams |
| Concentrated colour suspension (Opaspray K-1-2109) | 30 | milliliters |
| Polyvinylpyrrolidone (Povidone) | 5 | grams |
| Magnesium octadecanoate | 2.5 | grams |

Preparation of Tablet Core

A mixture of the A.I., the lactose and the starch is mixed well and thereafter humidified with a solution of the sodium dodecyl sulfate and the polyvinylpyrrolidone done in about 200 milliliters of water. The wet powder mixture is sieved, dried and sieved again. Then there is added the microcrystalline cellulose and the hydrogenated vegetable oil. The whole is mixed well and compressed into tablets.

Coating

To a solution of the methyl cellulose in 75 milliliters of denaturated ethanol there is added a solution of the ethyl cellulose in 150 milliliters of dichloromethane. Then there are added 75 milliliters of dichloromethane and the 1,2,3-propanetriol. The polyethylene glycol is molten and dissolved in 75 milliliters of dichloromethane. The latter solution is added to the former and then there are added the magnesium octadecanoate, the polyvinylpyrrolidone and the concentrated colour suspension and the whole is homogenated.

The tablet cores are coated with the thus obtained mixture in a coating apparatus.

Injectable Solution

The following formulation provides 1 liter of a parenteral solution comprising 4 mg of 3-[2-[4-(4-fluorobenzoyl)-1-piperidinyl]ethyl]-2,4(1H,3H)-quinazolinedione as the active ingredient per milliliter.

|  |  |  |
| --- | --- | --- |
| A.I. | 4 | grams |
| Lactic acid | 4 | grams |
| Propylene glycol | 0.05 | grams |
| Methyl 4-hydroxybenzoate | 1.8 | grams |
| Propyl 4-hydroxybenzoate | 0.2 | grams |
| Purified water q.s. ad 1 liter. | | |

The methyl and propyl 4-hydroxybenzoates are dissolved in about 0.5 liters of boiling water for injection. After cooling to about 50° C. there are added while stirring the lactic acid, the propylene glycol and the A.I.. The solution is cooled to room temperature and supplemented with water for injection q.s. ad volume. The solution is sterilized by filtration (U.S.P. XVII p. 811) and filled in sterile containers.

Suppositories

100 Suppositories each containing 20 mg of 3-[2-[4-(4-fluorobenzoyl)-1-piperidinyl]ethyl]-2,4(1H,3H)-quinazolinedione as the active ingredient are prepared from the following formulations:

|  |  |
| --- | --- |
| A.I. | 3 grams |
| 2,3-Dihydroxybutanedioic acid | 3 grams |
| Polyethylene glycol 400 | 25 milliliters |
| Surfactant (Span) | 12 grams |
| Triglycerides (Witepsol 555) q.s. ad 300 grams. | |

The A.I. is dissolved in a solution of the 2,3-dihydroxybutanedioic acid in the polyethylene glycol 400. The surfactant and the triglycerides are molten together. The latter mixture is mixed well with the former solution. The thus obtained mixture is poured into moulds at a temperature of 37°–38° C. to form the suppositories.

In view of the anti-congestive activity of the subject compounds, it is evident that the present invention provides a method of treating congestive diseases of warm-blooded animals by the systemic administration of an effective anti-congestive amount of a compound of formula (I) or of an intermediate of formula (XII) or a pharmaceutically acceptable acid addition salt thereof in admixture with a pharmaceutical carrier.

The following examples are intended to illustrate but not to limit the scope of the present invention. Unless otherwise stated all parts herein are by weight and all temperatures are in the centigrade scale.

(A) Preparation of Intermediates

EXAMPLE I

To 5 parts of magnesium are added 2.18 parts of 1,2-dibromoethane and a small amount of iodine to initiate the reaction. Then there is added dropwise a solution of 28 parts of 4-chloro-1-methylpiperidine in 180 parts of tetrahydrofuran while the mixture is heated to 70° C. After cooling, there is added dropwise a solution of 14 parts of 3-methylbenzonitrile in 90 parts of tetrahydrofuran. Upon completion, stirring is continued for 1 hour at reflux temperature. The reaction mixture is cooled and poured onto a solution of 75 parts of ammonium chloride in water. The product is extracted with 2,2'-oxybispropane. The extract is washed with water, dried, filtered and evaporated, yielding 35 parts of (3-methylphenyl) (1-methyl-4-piperidinyl)methanone as an oily residue.

Following the same procedure and using equivalent amounts of the appropriately substituted benzonitriles and 4-chloro-1-methylpiperidine there are also prepared:

(4-bromophenyl) (1-methyl-4-piperidinyl)methanone as a residue; and (2-chlorophenyl) (1-methyl-4-piperidinyl)methanone as an oily residue.

EXAMPLE II

To 7 parts of magnesium is added dropwise a solution of 50 parts of 1-bromo-2-methylbenzene in 140 parts of 1,1'-oxybisethane so that the mixture is refluxing. The whole is stirred for 15 minutes at reflux. The Grignard-complex is cooled to 10° C. and there is added dropwise a solution of 36 parts of 1-(phenylmethyl)-4-piperidinecarbonitrile in 70 parts of 1,1'-oxybisethane. Upon completion, stirring is continued for 4 hours at room temperature. The reaction mixture is decomposed with a solution of 40 parts of ammonium chloride in 400 parts of water. The organic phase is separated, dried, filtered and evaporated, yielding 31 parts of (2-methylphenyl) [1-(phenylmethyl)-4-piperidinyl]methanone as an oily residue.

EXAMPLE III

To a stirred mixture of 35 parts of (3-methylphenyl) (1-methyl-4-piperidinyl)methanone, 1 part of sodium carbonate and 225 parts of dimethylbenzene are added dropwise 22 parts of ethyl carbonochloridate at 20° C. Upon completion, stirring is continued for 6 hours at reflux temperature. The reaction mixture is evaporated, yielding 12 parts of ethyl 4-(3-methylbenzoyl)-1-piperidinecarboxylate as an oily residue.

In a similar manner there are also prepared starting from the corresponding phenyl(1-methyl or 1-phenylmethyl-4-piperidinyl)methanone:

ethyl 4-(4-bromobenzoyl)-1-piperidinecaboxylate as a residue;

ethyl 4-(2-chlorobenzoyl)-1-piperidinecarboxylate as an oily residue; and ethyl 4-(2-methylbenzoyl)-1-piperidinecarboxylate as an oily residue.

EXAMPLE IV

A mixture of 12 parts of ethyl 4-(3-methylbenzoyl)-1-piperidinecarboxylate and 225 parts of a hydrobromic acid solution 48% in water is stirred and refluxed for 3 hours. The reaction mixture is evaporated and the residue is crystallized from 2-propanol, yielding 7.5 parts of (3-methylphenyl) (4-piperidinyl)methanone hydrobromide.

Following the same hydrolysis-procedure there are also prepared:

(4-bromophenyl) (4-piperidinyl)methanone hydrobromide;

(2-chlorophenyl) (4-piperidinyl)methanone hydrobromide; mp. 200° C.; and (2-methylphenyl) (4-piperidinyl)methanone hydrobromide.

EXAMPLE V

A mixture of 25 parts of 2-chloropropanenitrile, 61 parts of (4-fluorophenyl)(4-piperidinyl)methanone hydrochloride, 63 parts of sodium carbonate and 160 parts of acetonitrile is stirred and refluxed (100° C.) overnight. The reaction mixture is cooled, water is added and the layers are separated. The aqueous phase is extracted with 4-methyl-2-pentanone. The combined organic phases are dried, filtered and evaporated. The residue is purified by column-chromatography over silica gel using a mixture of trichloromethane, hexane and methanol (50:49:1 by volume) as eluent. The pure fractions are collected and the eluent is evaporated. The solid residue is crystallized from 2,2'-oxybispropane. The product is filtered off, and dried yielding 17 parts of 4-(4-fluorobenzoyl)-α-methyl-1-piperidineacetonitrile; mp. 126.7° C.

A mixture of 32 parts of 4-(4-fluorobenzoyl)-α-methyl-1-piperidineacetonitrile and 400 parts of methanol, saturated with ammonia is hydrogenated in the Parr-apparatus at 25° C. with 5 parts of Raney-nickel catalyst. After the calculated amount of hydrogen is taken up, the catalyst is filtered off and the filtrate is evaporated. The residue is taken up in methylbenzene and the latter is evaporated again. The residue is dissolved in 2,2'-oxybispropane and the solution is filtered till clear. The solvent is evaporated, yielding 32 parts (100%) of [1-(2-amino-1-methylethyl)-4-piperidinyl] (4-fluorophenyl)methanone as an oily residue.

EXAMPLE VI

A mixture of 4.5 parts of 1-chloro-3,3-diethoxypropane, 12.15 parts of (4-fluorophenyl) (4-piperidinyl)methanone hydrochloride, 10.6 parts of sodium carbonate and 120 parts of 4-methyl-2-pentanone is stirred and refluxed overnight. The reaction mixture is cooled, water is added and the layers are separated. The organic phase is dried, filtered and evaporated. The residue is purified by column-chromatography over silica gel using a mixture of trichloromethane and methanol (95:5 by volume) as eluent. The pure factors are collected and the eluent is evaporated. The residue is crystallized from a mixture of methylbenzene and 2,2'-oxybispropane, yielding 9 parts (53%) of [1-(3,3-diethoxypropyl)-4-piperidinyl] (4-fluorophenyl)methanone.

EXAMPLE VII

A mixture of 50 parts of 2-amino-3,5-dichlorobenzoic acid and 240 parts of ethanol is saturated with gaseous hydrogen chloride. The whole is stirred and refluxed for 10 hours. The reaction mixture is allowed to cool and the solvent is evaporated. To the solid residue are added water and sodium hydroxide. The precipitated product is filtered off and dried, yielding 25 parts of ethyl 2-amino-3,5-dichlorobenzoate.

To a stirred mixture of 25 parts of ethyl 2-amino-3,5-dichlorobenzoate and 180 parts of dimethylbenzene are added dropwise 30 parts of ethyl carbonochloridate. Upon completion, stirring is continued for 8 hours at reflux temperature. The reaction mixture is evaporated and the residue is crystallized from petroleumether. The product is filtered off and dried, yielding 30 parts of ethyl 3,5-dichloro-2-(ethoxycarbonylamino)benzoate.

EXAMPLE VIII

A mixture of 40 parts of ethyl 4-chloro-2-[(ethoxycarbonyl)amino]benzoate and 10 parts of 2-aminoethanol is stirred and heated to 160°–170° C. while the formed ethanol is distilled off. After stirring for about 30 minutes, the mixture is cooled and 2-propanol is added. The solid product is filtered off and dried, yielding 23 parts (64%) of 7-chloro-3-(2-hydroxyethyl)-2,4(1H,3H)-quinazolinedione.

Following the same cyclization procedure and using equivalent amounts of the appropriately substituted 2-[(ethoxycarbonyl)amino]benzoates and 2-aminoethanol there are also prepared:

3-(2-hydroxyethyl)-1-methyl-2,4(1H,3H)-quinazolinedione;

6-chloro-3-(2-hydroxyethyl)-2,4(1H,3H)-quinazolinedione;

6,8-dichloro-3-(2-hydroxyethyl)-2,4(1H,3H)-quinazolinedione; and 3-(2-hydroxyethyl)-6-methyl-2,4(1H,3H)-quinazolinedione.

EXAMPLE IX

A mixture of 14 parts of 6-chloro-3,4-dihydro-3-(2-hydroxyethyl)-4-phenyl-2(1H)-quinazolinone, 5 parts of sodium acetate and 200 parts of methanol is hydrogenated at normal pressure and at room temperature with 2 parts of palladium-on-charcoal catalyst 10%. After the calculated amount of hydrogen is taken up, the catalyst is filtered off and the filtrate is evaporated. The residue is stirred in 2,2'-oxybispropane. The solid product is filtered off and stirred in 200 parts of water. It is filtered off again and dried, yielding 11.2 parts (91%) of 3,4-dihydro-3-(2-hydroxyethyl)-4-phenyl-2(1H)-quinazolinone; mp. 141° C.

EXAMPLE X

A mixture of 23 parts of 7-chloro-3-(2-hydroxyethyl)-2,4(1H,3H)-quinazolinedione, 32 parts of thionyl chloride and 150 parts of trichloromethane is stirred and refluxed for 4 hours. The reaction mixture is cooled. The precipitated product is filtered off, washed with trichloromethane and with petroleumether, and dried, yielding 22 parts (88%) of 7-chloro-3-(2-chloroethyl)-2,4(1H,3H)-quinazolinedione.

In a similar manner there are also prepared:

3-(2-chloroethyl)-1-methyl-2,4(1H,3H)-quinazolinedione;

3-(2-chloroethyl)-3,4-dihydro-4-phenyl-2(1H)-quinazolinone; mp. 179.5° C.

6-chloro-3-(2-chloroethyl)-3,4-dihydro-4-phenyl-2(1H)-quinazolinone;

6-chloro-3-(2-chloroethyl)-2,4(1H,3H)-quinazolinedone;

6,8-dichloro-3-(2-chloroethyl)-2,4(1H,3H)-quinazolinedone; mp. 207° C.; and 3-(2-chloroethyl)-6-methyl-2,4(1H,3H)-quinazolinedione.

EXAMPLE XI

A mixture of 13.6 parts of 2-aminobenzamide, 31.5 parts of 1-bromo-3-chloropropane, 21 parts of sodium carbonate and 200 parts of ethanol is stirred and refluxed over week-end. The reaction mixture is filtered and the filtrate is evaporated. The oily residue is stirred in methylbenzene. The mixture is filtered till clear and the solvent is evaporated. The oily residue is purified by column-chromatography over silica gel using a mixture of trichloromethane and methanol (95:5 by volume) as eluent. The pure fractions are collected and the eluent is evaporated. The solid residue is stirred in 2,2'-oxybispropane. The product is filtered off and dried, yielding 7 parts (33%) of 2-[(3-chloropropyl)amino]benzamide; mp. ±100° C.

EXAMPLE XII

A mixture of 10 parts of 2-[(3-chloropropyl)amino]benzamide, 16 parts of 2-propanone, 1 part of 4-methylbenzenesulfonic acid and 40 parts of ethanol is stirred and refluxed overnight. The reaction mixture is evaporated and the oily residue is stirred in 2,2'-oxybispropane. The product is filtered off and dried, yielding 10 parts of 1-(3-chloropropyl)-2,3-dihydro-2,2-dimethyl-4(1H)-quinazolinone.

EXAMPLE XIII

To a stirred and cooled (ice-bath) solution of 27.5 parts of 2-bromoethanamine hydrobromide in 200 parts of water is added a solution of 28.9 parts of 4-methoxy-2-nitrobenzoyl chloride in 63 parts of benzene at 5°–10° C. While stirring vigorously, there is added dropwise a solution of 10.8 parts of sodium hydroxide in 250 parts of water at 5°–10° C. Upon completion, stirring is continued for 2 hours at this temperature. The supernatant phase is decanted and the oily residue is stirred in 2-propanol. The product is filtered off and dried, yielding 27.5 parts (68%) of N-(2-bromoethyl)-4-methoxy-2-nitrobenzamide; mp. 133.8° C.

EXAMPLE XIV

To a stirred and cooled mixture of 25 parts of 2-aminoethanol and 135 parts of methylbenzene is added dropwise a solution of 29 parts of 4-fluoro-2-nitrobenzoyl chloride in methylbenzene. Upon completion, stirring is continued for 30 minutes at room temperature. The precipitated product is filtered off, taken up in water and extracted with 4-methyl-2-pentanone. The extract is dried, filtered and evaporated, yielding 28 parts (64%) of 4-fluoro-N-(2-hydroxyethyl)-2-nitrobenzamide as a residue.

A mixture of 28 parts of 4-fluoro-N-(2-hydroxyethyl)-2-nitrobenzamide, 40 parts of thionyl chloride and 150 parts of trichloromethane is stirred and refluxed for 2 hours. After cooling, the precipitated product is filtered off and dried, yielding 24.5 parts (83%) of N-(2-chloroethyl)-4-fluoro-2-nitrobenzamide.

EXAMPLE XV

A mixture of 14.4 parts of N-(3-bromopropyl)-2-nitrobenzamide, 12.2 parts of (4-fluorophenyl) (4-piperidinyl)methanone hydrochloride, 16 parts of sodium carbonate and 200 parts of 4-methyl-2-pentanone is stirred and refluxed for 3 hours using a water-separator. The reaction mixture is cooled, water is added and the layers are separated. The organic phase is dried, filtered and evaporated. The oily residue is purified by column-chromatography over silica gel using a mixture of trichloromethane and methanol (90:10 by volume) as eluent. The pure fractions are collected and the eluent is evaporated, yielding 18 parts (87%) of N-[3-[4-(4-fluorobenzoyl)-1-piperidinyl]propyl]-2-nitrobenzamide as an oily residue.

Following the same procedure and using equivalent amounts of (4-fluorophenyl) (4-piperidinyl)methanone hydrochloride and an appropriately substituted 2-nitrobenzamide there are also prepared:

N-[2-[4-(4-fluorobenzoyl)-1-piperidinyl]ethyl]-2-nitrobenzamide; mp. 150° C.;

4-fluoro-N-[2-[4-(4-fluorobenzoyl)-1-piperidinyl]ethyl]-2-nitrobenzamide; mp. 163.5° C.; and N-[2-[4-(4-fluorobenzoyl)-1-piperidinyl]ethyl]-4-methoxy-2-nitrobenzamide; mp. ±134° C.

EXAMPLE XVI

To 1 part of a solution of 2 parts of thophene in 40 parts of ethanol are added 18 parts of N-[3-[4-(4-fluorobenzoyl)-1-piperidinyl]propyl]-2-nitrobenzamide and 200 parts of methanol. The whole is hydrogenated at normal pressure and at room temperature with 2 parts of platinum-on-charcoal catalyst 5%. After the calculated amount of hydrogen is taken up, the catalyst is filtered off and the filtrate is evaporated. The oily residue is purified by column-chromatography over silica gel using a mixture of trichloromethane and methanol (90:10 by volume) as eluent. The pure fractions are collected and the eluent is evaporated. The oily residue is crystallized from 2-propanol. The product is filtered off and dried, yielding 7.5 parts (45%) of 2-amino-N-[3-[4-(4-fluorobenzoyl)-1-piperidinyl]propyl]benzamide; mp. 113.2° C. The mother liquor is evaporated, yielding a second fraction of 6 parts (36%) of 2-amino-N-[3-[4-(4-fluorobenzoyl)-1-piperidinyl]propyl]benzamide as an oily residue.

Following the same hydrogenating procedure there are also prepared:

2-amino-N-[2-[4-(4-fluorobenzoyl)-1-piperidinyl]ethyl]benzamide; mp 142.5° C.;

2-amino-4-fluoro-N-[2-[4-(4-fluorobenzoyl)-1-piperidinyl]ethyl]benzamide; mp. 124.1° C.; and 2-amino-N-[2-[4-(4-fluorobenzoyl)-1-piperidinyl]ethyl]-4-methoxybenzamide; mp. 168.1° C.

EXAMPLE XVII

A mixture of 7.2 parts of 2-[(4-chloro-1-oxobutyl)amino]benzamide, 7.3 parts of (4-fluorophenyl) (4-piperidinyl)methanone hydrochloride, 10.1 parts of N,N-diethylethanamine and 120 parts of acetonitrile is stirred and refluxed for 24 hours. The reaction mixture is evaporated and water is added to the residue. The oily product is extracted with trichloromethane. The extract is dried, filtered and evaporated, yielding 10 parts (81%) of N-[2-(aminocarbonyl)phenyl]-4-(4-fluorobenzoyl)-1-piperidinebutanamide as a residue.

EXAMPLE XVIII

A. To a stirred mixture of 250 parts of pyridine and 39 parts of 6-fluoro-1H-indole are added dropwise 42 parts of benzoyl chloride at 22° C. Upon completion, stirring is continued for 2 hours at room temperature. The reaction mixture is diluted with water and a hydrochloric acid solution 2 N is added. The product is extracted twice with 350 parts of 1,1'-oxybisethane. The combined extracts are dried, filtered and evaporated. The residue is purified by column-chromatography over silica gel using a mixture of trichloromethane and methanol (95:5 by volume) as eluent. The pure fractions are collected and the eluent is evaporated, yielding 95 parts of 1-benzoyl-4-(6-fluoro-1H-indol-3-yl)-1,4-dihydropyridine as an oily residue.

B. A mixture of 95 parts of 1-benzoyl-4-(6-fluoro-1H-indol-3-yl)-1,4-dihydropyridine and 540 parts of N,N-dimethylacetamide is hydrogenated in the Parr-apparatus with 5 parts of palladium-on-charcoal catalyst 10%. After the calculated amount of hydrogen is taken up, the catalyst is filtered off over Hyflo and the filtrate is poured onto water while stirring: an oil is precipitated. The supernatant aqueous phase is decanted and the residual oil is washed with water. The oily product is extracted with trichloromethane. The extract is dried, filtered and evaporated. The residue is washed successively with a mixture of petroleumether and 2,2'-oxybispropane, with a hydrochloric acid solution 2 N and with water, and dissolved in trichloromethane. The latter is washed with a sodium hydroxide solution 1 N and with water, dried, filtered and evaporated. The residue is heated in a small amount of N,N-dimethylacetamide at 80° C. and the mixture is allowed to stand over week-end. The solid product is filtered off, washed with a mixture of water and ethanol, and dried in vacuo at 80° C., yielding 25 parts of 1-benzoyl-4-(6-fluoro-1H-indol-3-yl)-piperidine; mp. 220° C.

C. A mixture of 24 parts of 1-benzoyl-4-(6-fluoro-1H-indol-3-yl)-piperidine, 70 parts of potassium hydroxide, 495 parts of 1,2-ethanediol and 80 parts of water is stirred and refluxed for 6 hours. The reaction mixture is cooled and 500 parts of water are added while stirring. The precipitated product is filtered off, washed with water and petroleumether and dried in vacuo at 80° C., yielding 16 parts of 6-fluoro-3-(4-piperidinyl)-1H-indole; mp. 224° C.

D. A mixture of 7.5 parts of 3-(2-chloroethyl)-2,4(1H,3H)-quinazolinedione, 6.8 parts of 6-fluoro-3-(4-piperidinyl)-1H-indole, 10 parts of sodium carbonate, 0.1 parts of potassium iodide and 240 parts of 4-methyl-2-pentanone is stirred and refluxed overnight. Water is added and the layers are separated. The aqueous phase is set aside. The organic phase is dried, filtered and evaporated. The solid residue is boiled in 2-propanol. The product is filtered off and dried, yielding a first fraction of 4 parts of 3-[2-[4-(6-fluoro-1H-indol-3-yl)-1-piperidinyl]ethyl]-2,4(1H,3H)-quinazolinedione. From the aqueous phase (see above), a solid product is filtered off and boiled in 2-propanol. The product is filtered off and dried, yielding a second fraction of 3 parts of 3-[2-[4-(6-fluoro-1H-indol-3-yl)-1-piperidinyl]ethyl]-2,4(1H,3H)-quinazolinedione; mp. 300.6° C.

E. Ozonised oxygen is bubbled through a stirred mixture of 6 parts of 3-[2-[4-(6-fluoro-1H-indol-3-yl)-1-piperidinyl]ethyl]-2,4-(1H,3H)-quinazolinedione and 100 parts of acetic acid till a clear solution is obtained. Then there are added 200 parts of crushed ice and 100 parts of water and the whole is alkalized with a sodium hydroxide solution. The product is extracted with trichloromethane and a small amount of ethanol. The extract is dried, filtered and evaporated, yielding 2.3 parts of N-[2-[1-[2-(1,4-dihydro-2,4-dioxo-3(2H)-quinazolinyl)ethyl]-4-piperidinylcarbonyl]-5-fluorophenyl]formamide as a residue.

EXAMPLE XIX

A mixture of 13.5 parts of 1-(2-aminophenyl)ethanone, 12.1 parts of N,N-diethylethanamine and 72 parts of benzenes are stirred and cooled at 5°–10° C. Then there is added dropwise a solution of 18.2 parts of trichloroacetyl chloride in 36 parts of benzene while still cooling at 1°–10° C. Upon completion, stirring at that temperature is continued for 30 minutes. The reaction mixture is filtered, the filter-cake is washed with benzene and the filtrate is evaporated. The solid residue is boiled in methanol. After cooling, the product is filtered off and dried, yielding 19 parts (68%) of N-(2-acetylphenyl)-2,2,2-trichloroacetamide; mp. 112.7° C.

A mixture of 60 parts of N-(2-acetylphenyl)-2,2,2-trichloroacetamide, 14 parts of 2-aminoethanol and 200 parts of ethanol is stirred first for 5.50 hours at reflux and further overnight while the temperature is allowed to cool to room temperature. The formed precipitate is filtered off. The product is washed with 2,2'-oxybispropane and dried in vacuo, yielding 40 parts (59%) of 2,2,2-trichloro-N-[2-[1-[(2-hydroxyethyl)imino]ethyl]phenyl]acetamide; mp. 182° C.

To 135 parts of N,N-dimethylforamide are added first 16.2 parts of 2,2,2-trichloro-N-[2-[1-[(2-hydroxyethyl)imino]ethyl]phenyl]acetamide and then portionwise 5.7 parts of sodium borohydride while stirring: exothermic reaction. Upon completion, stirring is continued overnight at room temperature. The reaction mixture is poured onto water and the product is extracted with trichloromethane. The extract is dried, filtered and evaporated. The residue is purified by column-chromatography over silica gel using a mixture of trichloromethane and methanol (90:10 by volume) as eluent. The pure fractions are collected and the eluent is evaporated, yielding 8.5 parts of 3,4-dihydro-3-(2-hydroxyethyl)-4-methyl-2(1H)-quinazolinone as a solid residue.

A mixture of 8 parts of 3,4-dihydro-3-(2-hydroxyethyl)-4-methyl-2(1H)-quinazolinone, 8 parts of thionyl chloride and 90 parts of trichloromethane is stirred and refluxed for 1.50 hours. The reaction mixture is evaporated. The residue is purified by column-chromatography over silica gel using a mixture of trichloromethane and methanol (95:5 by volume) as eluent. The pure fractions are collected and the eluent is evaporated. The residue is stirred in 2,2'-oxybispropane. The product is filtered off and dried, yielding 6.6 parts of 3-(2-chloroethyl)-3,4-dihydro-4-methyl-2(1H)-quinazolinone; mp. 126.4° C.

EXAMPLE XX

To a stirred mixture of 10 parts of methyl 2-[(2-hydroxyethyl)amino]benzoate and 100 parts of acetic acid is added dropwise a solution of 4.5 parts of potassium cyanate in 25 parts of water. Upon completion, stirring at room temperature is continued overnight. The reaction mixture is evaporated. The solid residue is stirred with water. The product is filtered off, washed with water and ethanol, and dried, yielding 5 parts (48%) of 1-(2-hydroxyethyl)-2,4(1H,3H)-quinazolinedione; mp. 273.6° C.

A mixture of 3.6 parts of 1-(2-hydroxyethyl)-2,4(1H,3H)-quinazolinedione and 40 parts of thionyl chloride is stirred and refluxed overnight. The reaction mixture is allowed to cool to room temperature. The precipitated product is filtered off, washed with 2,2'-oxybispropane and dried, yielding 3.4 parts (86%) of 1-(2-chloroethyl)-2,4-(1H,3H)-quinazolinedione; mp. 215.3° C.

Following the same procedure and using equivalent amounts of the appropriate starting materials there are also prepared:

1-(3-hydroxypropyl)-2,4(1H,3H)-quinazolinedione; mp. 240° C.; and
1-(3-chloropropyl)-2,4(1H,3H)-quinazolinedione; mp. 187.1° C.

EXAMPLE XXI

To a stirred mixture of 18 parts of 2-phenyl-4(3H)-quinazolinone and 225 parts of N,N-dimethylformamide are added portionwise at room temperature 3.2 parts of sodium hydride dispersion 60% (exothermic reaction: the temperature rises to 34° C.). After the addition is complete, the whole is stirred for 10 minutes whereafter 12.4 parts of 2-bromoethanol are added dropwise (slightly exothermic). Upon completion, stirring is continued first for one hour at room temperature, then for 2 hours at 80° C. and further overnight at room temperature. The reaction mixture is cooled, poured onto water and the solid product is sucked off. It is washed with water and 2,2'-oxybispropane and dried in vacuo at 60° C., yielding 15 parts of 3-(2-hydroxyethyl)-2-phenyl-4(3H)-quinazolinone.

To a stirred mixture of 15 parts of 3-(2-hydroxyethyl)-2-phenyl-4(3H)-quinazolineone and 375 parts of trichloromethane are added dropwise 24 parts of thionyl chloride at room temperature. Upon completion, stirring is continued for 2 hours at reflux. The reaction mixture is evaporated. Water is added to the residue and the whole is neutralized with a sodium hydrogen carbonate solution. The product is extracted with trichloromethane. The extract is washed with water, dried, filtered and evaporated. The residue is crystallized from a mixture of 2,2'-oxybispropane and petroleumether. The product is filtered off and dried, yielding 11.6 parts of 3-(2-chloroethyl)-2-phenyl-4(3H)-quinazolinone.

A mixture of 5.5 parts of 3-(2-chloroethyl)-2-phenyl-4(3H)-quinazolinone, 3.2 parts of 3-(4-piperidinyl)-1H-indole, 7 parts of sodium carbonate, 0.1 parts of potassium iodide and 200 parts of 4-methyl-2-pentanone is stirred and refluxed for 22 hours. The reaction mixture is filtered over Hyflo and the filtrate is evaporated. The residue is purified by column-chromatography over silic gel using a mixture of trichloromethane and methanol (92:8 by volume) as eluent. The pure fractions are collected and the eluent is evaporated. The residue is crystallized from a mixture of ethanol and 1,1'-oxybisethane, yielding 5 parts of 3-[2-[4-(1H-indol-3-yl)-1-piperidinyl]ethyl]-2-phenyl-4(3H)-quinazolinone; mp. 191.3° C.

EXAMPLE XXII

To a stirred mixture of 80 parts of sodium methoxide and 160 parts of methanol are added successively 50 parts of 2-thiopheneacetonitrile and then dropwise 66 parts of 1-(phenylmethyl)-4-piperidinone. Upon completion, the whole is heated to reflux and stirring at reflux temperature is continued for one hour. The reaction mixture is cooled and evaporated. The residue is distilled in a molecular distillation-apparatus, yielding about 70 parts of α-[1-(phenylmethyl)-4-piperidinylidene]-2-thiopheneacetonitrile as a residue.

A mixture of 70 parts of α-[1-(phenylmethyl)-4-piperidinylidene]-2-thiopheneacetonitrile in 800 parts of methanol is hydrogenated at normal pressure and at room temperature with 10 parts of palladium-on-charcoal catalyst 10%. Upon the calculated amount of hydrogen is taken up, the catalyst is filtered off and the filtrate is evaporated, yielding 70 parts of 1-(phenylmethyl)-α-(2-thienyl)-4-piperidineacetonitrile as a residue.

To a stirred mixture of 29.6 parts of 1-(phenylmethyl)-α-(2-thienyl)-4-piperidineacetonitrile in 100 parts of dimethyl sulfoxide are added portionwise 4 parts of sodium hydride dispersion 60%. Upon completion, stirring is continued overnight. The reaction mixture is poured onto water. The precipitated product is sucked off and extracted with trichloromethane. The extract is dried, filtered and evaporated. The residue is crystallized from 2,2'-oxybispropane, yielding 10 parts (35%) of [1-(phenylmethyl)-4-piperidinyl] (2-thienyl) methanone; mp. 100.5° C.

To a stirred mixture of 15 parts of [1-(phenylmethyl)-4-piperidinyl] (2-thienyl)methanone in 120 parts of benzene are added dropwise 8 parts of ethyl carbonochloridate. Upon completion, the whole is heated to reflux and stirred for 6 hours at reflux temperature. The reaction mixture is cooled, filtered and evaporated, yielding 13 parts of ethyl 4-(2-thienylcarbonyl)-1-piperidinecarboxylate as a residue.

A mixture of 20 parts of ethyl 4-(2-thienylcarbonyl)-1-piperidinecarboxylate and 120 parts of hydrobromic acid solution 48% in water is stirred and refluxed for 2 hours. The reaction mixture is cooled and the precipitated product is filtered off. It is washed with 2-propanol and dried, yielding 17 parts (85%) of (4-piperidinyl) (2-thienyl)methanone hydrobromide.

(b) Preparation of Final Compounds

EXAMPLE XXIII

A mixture of 4.5 parts of 3-(2-chloroethyl)-2,4(1H,3H)-quinazolinedione, 4.9 parts of (4-fluorophenyl) (4-piperidinyl) methanone hydrochloride, 8 parts of sodium carbonate and 80 parts of 4-methyl-2-pentanone is stirred and refluxed overnight. The reaction mixture is cooled and water is added. The precipitated product is filtered off and crystallized from 4-methyl-2-pentanone, yielding, after drying, 2,2 parts (27%) of 3-[2-[4-(4-fluorobenzoyl)-1-piperidinyl]ethyl]-2,4-(1H,3H)-quinazolinedione; mp. 227°-235° C.

Following the same procedure and using equivalent amounts of the appropriate starting materials there are also prepared:

| $(R^1)_n$ | $R^3$ | Alk | R | X | Ar | Base or Salt | Melting Point in °C. |
|---|---|---|---|---|---|---|---|
| — | H | $(CH_2)_3$ | H | CO | $4\text{-}F\text{—}C_6H_4$ | — | 187.2 |
| — | H | $(CH_2)_2$ | H | CO | $4\text{-}Cl\text{—}C_6H_4$ | — | 259 |
| — | H | $(CH_2)_2$ | H | CO | $4\text{-}OCH_3\text{—}C_6H_4$ | — | 236.5 |
| — | H | $(CH_2)_2$ | H | CO | $4\text{-}CH_3\text{—}C_6H_4$ | — | 211.7 |
| 7-Cl | H | $(CH_2)_2$ | H | CO | $4\text{-}F\text{—}C_6H_4$ | — | 235.2 |
| — | $CH_3$ | $(CH_2)_2$ | H | CO | $4\text{-}F\text{—}C_6H_4$ | HCl | 248.1 |
| — | H | $(CH_2)_2$ | H | CO | $3\text{-}CF_3\text{—}C_6H_4$ | — | 182.6–184.6 |
| — | H | $(CH_2)_2$ | H | CO | $3\text{-}CH_3\text{—}C_6H_4$ | — | 171 |
| — | H | $(CH_2)_2$ | H | CO | $4\text{-}Br\text{—}C_6H_4$ | — | 251.5 |
| 6,8-$Cl_2$ | H | $(CH_2)_2$ | H | CO | $4\text{-}F\text{—}C_6H_4$ | — | 211 |
| — | H | $(CH_2)_2$ | H | CO | $2\text{-}Cl\text{—}C_6H_4$ | — | 162.5 |
| — | H | $(CH_2)_2$ | H | —C—(O O) | $4\text{-}F\text{—}C_6H_4$ | — | 204.5 |
| — | H | $(CH_2)_2$ | H | $CH_2$ | $4\text{-}F\text{—}C_6H_4$ | — | 193.4 |
| — | H | $(CH_2)_2$ | 4-OH | CO | $4\text{-}F\text{—}C_6H_4$ | — | 255.2 |
| 6-Cl | H | $(CH_2)_2$ | H | CO | $4\text{-}F\text{—}C_6H_4$ | — | 222.2–223 |
| 6-$CH_3$ | H | $(CH_2)_2$ | H | CO | $4\text{-}F\text{—}C_6H_4$ | — | 205.5 |
| — | H | $(CH_2)_2$ | H | CO | $C_6H_5$ | — | 214.5 |
| — | H | $(CH_2)_2$ | H | CO | $2\text{-}CH_3\text{—}C_6H_4$ | — | 193.8 |
| — | H | $(CH_2)_2$ | H | CO | 2-thienyl | — | 266.9 |

EXAMPLE XXIV

A mixture of 6 parts of 3-(2-chloroethyl)-1-phenyl-2,4(1H,3H)-quinazolinedione, 8.3 parts of (4-fluorophenyl) (4-piperidinyl)methanone and 48 parts of ethanol is stirred and refluxed. N,N-dimethylformamide is added at reflux temperature till all solid enters solution. Stirring is continued overnight at reflux. The reaction mixture is evaporated. The residue is purified twice by column-chromatography over silica gel using first a mixture of trichloromethane and methanol (95:5 by volume) and then a mixture of trichloromethane and methanol (98:2 by volume) as eluent. The pure fractions are collected and the eluent is evaporated. The residue is crystallized from 2-propanol, yielding 2.2 parts (23%) of 3-[2-[4-(4-fluorobenzoyl)-1-piperidinyl]ethyl]-1-phenyl-2,4(1H,3H)-quinazolinedione; mp. 166.1° C.

EXAMPLE XXV

A mixture of 5.8 parts of 6-chloro-3-(2-chloroethyl)-3,4-dihydro-4-phenyl-2(1H)-quinazolinone, 7.4 parts of (4-fluorophenyl) (4-piperidinyl)methanone and 56 parts of ethanol is stirred and refluxed overnight. The reaction mixture is evaporated. The residue is purified by column-chromatography over silica gel using a mixture of trichloromethane and methanol (95:5 by volume) as eluent. The pure fractions are collected and the eluent is evaporated. The oily residue solidifies on triturating in 2,2′-oxybispropane. The product is filtered off and dried, yielding 5 parts (57%) of 6-chloro-3-[2-[4-(4-fluorobenzoyl)-1-piperidinyl]ethyl]-3,4-dihydro-4-phenyl-2(1H)-quinazolinone; mp. 196° C.

In a similar manner there are also prepared:

3-[2-[4-(4-fluorobenzoyl)-1-piperidinyl]ethyl]-3,4-dihydro-4-phenyl-2(1H)-quinazolinone; mp. 173.3° C.; and 3-[2-[4-(4-fluorobenzoyl)-1-piperidinyl]ethyl]-3,4-dihydro-4-methyl-2(1H)-quinazolinone; mp. 172° C.

EXAMPLE XXVI

A mixture of 3.6 parts of 1-(3-chloropropyl)-2,4(1H,3H)-quinazolinedione, 3.02 parts of (4-fluorophenyl)(4-piperidinyl)methanone hydrochloride, 3.7 parts of sodium carbonate, 0.1 parts of potassium iodide and 120 parts of 4-methyl-2-pentanone is stirred and refluxed overnight using a water-separator. The reaction mixture is cooled, water is added and the layers are separated. The organic phase is dried, filtered and concentrated to a small volume. After cooling the concentrate, the precipitated product is filtered off and crystallized from 2-propanol, yielding 1.3 parts (18.5%) of 1-[3-[4-(4-fluorobenzoyl)-1-piperidinyl]propyl]-2,4(1H,3H)-quinazolinedione; mp. 192.9° C.

Following the same procedure and starting from 1-(2-chloroethyl)-2,4(1H,3H)-quinazolinedione there is also prepared:

1-[2-[4-(4-fluorobenzoyl)-1-piperidinyl]ethyl]-2,4(1H,3H)-quinazolinedione; mp. 219.7° C.

EXAMPLE XXVII

A mixture of 5.6 parts of 1-(3-chloropropyl)-2,3-dihydro-2,2-dimethyl-4(1H)-quinazolinone, 4.9 parts of (4-fluorophenyl) (4-piperidinyl)methanone hydrochloride, 10 parts of sodium carbonate, 0.1 parts of potassium iodide and 200 parts of 4-methyl-2-pentanone is stirred and refluxed overnight with water-separator. The reaction mixture is cooled, water is added and the layers are separated. The 4-methyl-2-pentanone phase is dried, filtered and evaporated. The solid residue is purified by column-chromatography over silica gel using a mixture of trichloromethane and methanol (95:5 by volume) as eluent. The pure fractions are collected and the eluent is evaporated. The solid residue is stirred in 2,2′-oxybispropane. The product is filtered off and dried, yielding 6.6 parts (78%) of 1-[3-[4-(4-fluorobenzoyl)-1-piperidinyl]propyl]-2,3-dihydro-2,2-dimethyl-4(1H)-quinazolinone; mp. 185.7° C.

EXAMPLE XXVIII

A mixture of 5.5 parts of 3-(2-chloroethyl)-2-phenyl-4(3H)-quinazolinone, 4 parts of (4-fluorophenyl)(4-piperidinyl)methanone hydrochloride, 7 parts of sodium carbonate, 0.1 parts of potassium iodide and 200 parts of 4-methyl-2-pentanone is stirred and refluxed for 24 hours using a water-separator. The reaction mixture is filtered while hot. The filtrate is evaporated. The residue is purified by column-chromatography over silica gel using a mixture of trichloromethane and methanol (95:5 by volume) as eluent. The pure fractions are collected and the eluent is evaporated. The residue is crystallized from a mixture of ethanol and 1,1′-oxybisethane. The product is filtered off and dried, yielding 5 parts (69%) of 3-[2-[4-(4-fluorobenzoyl)-1-piperidinyl]ethyl]-2-phenyl-4(3H)-quinazolinone; mp. 143.8° C.

EXAMPLE XXIX

A mixture of 10 parts of N-[2-(aminocarbonyl)-phenyl]-4-(4-fluorobenzoyl)-1-piperidinebutanamide, 60 parts of sodium hydroxide solution 2 N and 80 parts of ethanol is stirred and refluxed for 1.50 hours. The reaction mixture is evaporated and water is added to the residue. The oily product is dissolved in trichloromethane. The solution is dried, filtered and evaporated. The residue is crystallized twice from 4-methyl-2-pentanone. The product is filtered off and dried, yielding 1 part (10.5%) of 2-[3-[4-(4-fluorobenzoyl)-1-piperidinyl]-propyl]-4(3H)-quinazolinone; mp. 184° C.

EXAMPLE XXX

A mixture of 7 parts of 2-amino-N-[3-[4-(4-fluorobenzoyl)-1-piperidinyl]propyl]benzamide, 12 parts of formic acid and 135 parts of methylbenzene is stirred and refluxed for 1 hour. Stirring at reflux is continued for 1 hour using a water-separator. The solvent is evaporated. The oily residue is purified by column-chromatography over silica gel using a mixture of trichloromethane and methanol (90:10 by volume) as eluent. The pure fractions are collected and the eluent is evaporated. The residue is converted into the (E)-2-butenedioate salt in 2-propanol. The salt is filtered off and dried, yielding 5 parts (54%) of 3-[3-[4-(4-fluorobenzoyl)-1-piperidinyl]propyl]-4(3H)-quinazolinone (E)-2-butenedioate (1:1); mp. 201.1° C.

Following the same procedure and starting from 2-amino-N-[2-[4-(4-fluorobenzoyl)-1-piperidinyl]ethyl]-benzamide there is also prepared:

3-[2-[4-(4-fluorobenzoyl)-1-piperidinyl]ethyl]-4(3H)-quinazolinone; mp. 139.2° C.

EXAMPLE XXXI

A mixture of 6.5 parts of 2-amino-N-[2-[4-(4-fluorobenzoyl)-1-piperidinyl]ethyl]benzamide, 0.5 parts of paraformaldehyde, 3 drops of sodium hydroxide solution 50%, 80 parts of ethanol and 10 parts of water is stirred and refluxed overnight. The reaction mixture is allowed to cool to room temperature while stirring. The precipitated product if filtered off, washed with ethanol and crystallized from 200 parts of ethanol, yielding 3.3 parts (50%) of 3-[2-[4-(4-fluorobenzoyl)-1-piperidinyl]ethyl]-2,3-dihydro-4(1H)-quinazolinone; mp. 203.4° C.

Following the same procedure and starting from 2-amino-N-[3-[4-(4-fluorobenzoyl)-1-piperidinyl]-propyl]benzamide there is also prepared:

3-[3-[4-(4-fluorobenzoyl)-1-piperidinyl]propyl]-2,3-dihydro-4-(1H)-quinazolinone (E)-2-butenedioate (1:1); mp. 188.2° C.

EXAMPLE XXXII

A mixture of 6 parts of 2-amino-N-[2-[4-(4-fluorobenzoyl)-1-piperidinyl]ethyl]benzamide, 10 parts of acetic acid anhydride and 108 parts of methylbenzene is stirred and refluxed overnight. The reaction mixture is evaporated and water is added to the oily residue. The whole is alkalized with a dilute sodium hydroxide solution and extracted with trichloromethane. The extract is dried, filtered and evaporated. The oily residue is crystallized from a mixture of 4-methyl-2-pentanone and 2,2′-oxybispropane. The product is filtered off and recrystallized from 2-propanol, yielding 4.4 parts (69%) of 3-[2-[4-(4-fluorobenzoyl)-1-piperidinyl]ethyl]-2-methyl-4(3H)-quinazolinone; mp. 164.9° C.

EXAMPLE XXXIII

A mixture of 9 parts of 2-aminobenzenecarboxamide, 12 parts of concentrated hydrochloric acid and 120 parts of absolute ethanol is stirred and refluxed for 2 hours. Then there are added 3.6 parts of [1-(3,3-diethoxypropyl)-4-piperidinyl](4-fluorophenyl) methanone and stirring at reflux is continued overnight. The reaction mixture is evaporated and the residue is stirred with water. The whole is alkalized with ammonia and the product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is crystallized twice from 4-methyl-2-pentanone, yielding 1.9 parts (19%) of 2-[2-[4-(4-fluorobenzoyl)-1-piperidinyl]ethyl]-2,3-dihydro-4(1H)-quinazolinone; mp. 153.4° C.

EXAMPLE XXXIV

A mixture of 6.7 parts of methyl 2-isothiocyanatobenzoate, 8 parts of [1-(2-amino-1-methylethyl)-4-piperidinyl](4-fluorophenyl)methanone and 108 parts of tetrahydrofuran is stirred overnight at room temperature. The reaction mixture is evaporated. The residue is purified twice by column-chromatography over silica gel using first a mixture of trichloromethane and methanol (90:10 by volume) and then a mixture of trichloromethane and methanol (95:5 by volume) as eluent. The pure fractions are collected and the eluent is evaporated. The residue is crystallized twice from 2-propanol, yielding 1.6 parts (13%) of 3-[2-[4-(4-fluorobenzoyl)-1-piperidinyl]propyl]-2,3-dihydro-2-thioxo-4(1H)-quinazolinone; mp. 160.6° C.

EXAMPLE XXXV

A mixture of 2.2 parts of 2-amino-4-fluoro-N-[2-[4-(4-fluorobenzoyl)-1-piperidinyl]ethyl]benzamide, 1.2 parts of 1,1'-bis[1H-imidazol-1-yl]methanone and 45 parts of tetrahydrofuran is stirred and refluxed for 3 hours. The reaction mixture is cooled and the solvent is evaporated. The residue is boiled in 4-methyl-2-pentanone. The solid product is filtered off and crystallized from N,N-dimethylformamide, yielding 0.8 parts (30%) of 7-fluoro-3-[2-[4-(4-fluorobenzoyl)-1-piperidinyl]ethyl]-2,4(1H,3H)-quinazolinedione; mp. 248° C.

In a similar manner there is also prepared:
3-[2-[4-(4-fluorobenzoyl)-1-piperidinyl]ethyl]-7-methoxy-2,4(1H,3H)-quinazolinedione; mp. 245.4° C.

EXAMPLE XXXVI

To a stirred solution of 6.5 parts of 2-amino-N-[3-[4-(4-fluorobenzoyl)-1-piperidinyl]propyl]benzamide in 63 parts of tetrahydrofuran are added 3 parts of 1,1'-bis[1H-imidazol-1-yl]methanethione at room temperature. Stirring is continued for 1 hour at room temperature. The reaction mixture is filtered till clear and the solvent is evaporated. The oily residue is stirred in a mixture of water and 2,2'-oxybispropane. The precipitated product is filtered off and crystallized from a mixture of N,N-dimethylformamide, water and a small amount of ethanol, yielding 5.6 parts (78%) of 3-[3-[4-(4-fluorobenzoyl)-1-piperidinyl]propyl]-2,3-dihydro-2-thioxo-4(1H)-quinazolinone; mp. 200.2° C.

In a similar manner there is also prepared:
3-[2-[4-(4-fluorobenzoyl)-1-piperidinyl]ethyl]-2,3-dihydro-2-thioxo-4(1H)-quinazolinone; mp. 225.5° C.

EXAMPLE XXXVII

A mixture of 2.3 parts of N-[2-[1-[2-(1,4-dihydro-2,4-dioxo-3(2H)-quinazolinyl)ethyl]-4-piperidinylcarbonyl]-5-fluorophenyl]formamide, 33 parts of concentrated sulfuric acid and 144 parts of ethanol is stirred and refluxed for 1 hour. The reaction mixture is poured onto crushed ice and alkalized with a dilute sodium hydroxide solution. The precipitated product is filtered off and crystallized from 4-methyl-2-pentanone, yielding 0.4 parts of 3-[2-[4-(2-amino-4-fluorobenzoyl)-1-piperidinyl]ethyl]-2,4(1H,3H)-quinazolinedione; mp. 269.5° C.

EXAMPLE XXXVIII

To a stirred mixture of 2.6 parts of 3-[2-[4-(4-fluorobenzoyl)-1-piperidinyl]ethyl]-2,4-(1H,3H)-quinazolinedione and 120 parts of methanol are added portionwise 2 parts of sodium borohydride. Upon completion, stirring is continued overnight at room temperature. Water is added and the whole is evaporated. The residue is stirred in water. The solid product is filtered off and crystallized from 2-propanone, yielding 1.2 parts of 3-[2-[4-[(4-fluorophenyl)hydroxymethyl]-1-piperidinyl]ethyl]-2,4(1H,3H)-quinazolinedione; mp. 212.8° C.

EXAMPLE XXXIX

A mixture of 5 parts of 3-(2-chloroethyl)-2,4(1H,3H)-quinazolinedione, 6 parts of α-(4-fluorophenyl)-4-piperidinemethanol acetate (ester) hydrochloride, 8 parts of sodium carbonate and 280 parts of 4-methyl-2-pentanone is stirred and refluxed overnight. The reaction mixture is filtered and the filtrate is evaporated. The oily residue is purified by column-chromatography over silica gel using a mixture of trichloromethane and methanol (95:5 by volume) as eluent. The pure fractions are collected and the eluent is evaporated. The residue is crystallized from 4-methyl-2-pentanone, yielding 2.3 parts of 1-[2-(1,4-dihydro-2,4-dioxo-3(2H)-quinazolinyl)ethyl]-α-(4-fluorophenyl)-4-piperidinemethanol acetate (ester); mp. 185.2° C.

EXAMPLE XL

Following the procedure described in Example XXV and using equivalent amounts of the appropriate starting materials there is also prepared:
3,4-dihydro-3-[2-[4-(4-fluorobenzoyl)-1-piperidinyl]ethyl]-2(1H)-quinazolinone; mp. 182.1° C.

EXAMPLE XLI

Following the procedure described in Example XXIII and using equivalent amounts of the appropriate starting materials there is also prepared:
3-[2-[4-(3-pyridinylcarbonyl)-1-piperidinyl]ethyl]-2,4(1H,3H)-quinazolinedione.

EXAMPLE XLII

Following the procedure described in Example XVIII-D and using equivalent amounts of the appropriate starting materials there is also prepared:
3-[2-[4-(1H-indol-3-yl)-1-piperidinyl]ethyl]-2,4(1H,3H)-quinazolinedione; mp. 291.2° C.

What is claimed is:
1. A chemical compound selected from the group consisting of a quinazoline compound having the formula

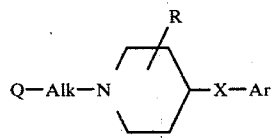

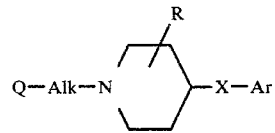

and the pharmaceutically acceptable acid addition salts thereof, wherein;

Ar is a number selected from the group consisting of aryl, thienyl, and pyridinyl radicals;

X is a member selected from the group consisting of

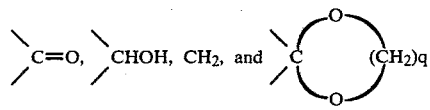

wherein said q is the integer 2 or 3;

R is a member selected from the group consisting of hydrogen, hydroxy and lower alkyl;

Alk is an alkylene chain having from 1 to 4 carbon atoms; and

Q is a quinazolinyl radical, the 1-, 2-, 3- or 4-position of which is connected with the alkylene side chain, said quinazolinyl radical bearing in one or both of its 2- and 4-positions a oxo or thioxo group, wherein the benzene ring of said quinazolinyl radical is optionally substituted with 1 to 3 substituents each independently selected from the group consisting of halo, lower alkyl, lower alkyloxy, trifluoromethyl, nitro and cyano, and wherein the pyrimidino ring of said quinazolinyl radical may be partly or fully saturated, said pyrimidino ring being optionally substituted with 1 to 3 substituents independently selected from the group consisting of lower alkyl, aryl, aryl(lower alkyl), thienyl, pyridinyl, thienyl(loweralkyl), and pyridinyl (loweralkyl);

wherein said aryl as used in the definition of said Ar and of said Q is a member selected from the group consisting of phenyl substituted with from 1 to 2 substituents each independently selected from the group consisting of halo, lower alkyl, lower alkyloxy, trifluoromethyl and amino.

2. A chemical compound according to claim 1 wherein X is CO.

3. A chemical compound according to claim 2 wherein Alk is an 1,2-ethanediyl radical.

4. A chemical compound selected from the group consisting of 3-[2-[4-(4-fluorobenzoyl)-1-piperidinyl]ethyl]-2,4(1H,3H)-quinazolinedione and the pharmaceutically acceptable acid addition salts thereof.

5. A chemical compound according to claim 1 wherein Ar is an aryl radical, X is >C=O, Alk is an alkylene chain having 2 or 3 carbon atoms; and Q is connected to the alkylene side chain by the 2- or 3-position.

6. An anti-congestive composition comprising an inert carrier and as an active ingredient an effective anticongestive amount of a chemical compound selected from the group consisting of a quinazoline compound having the formula and the pharmaceutically acceptable acid addition salts thereof, wherein:

Ar is a member selected from the group consisting of aryl, thienyl, and pyridinyl radicals;

X is a member selected from the group consisting of

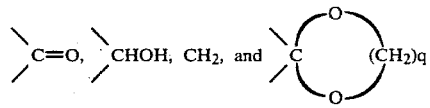

wherein said q is the integer 2 or 3;

R is a member selected from the group consisting of hydrogen, hydroxy and lower alkyl;

Alk is an alkylene chain having from 1 to 4 carbon atoms; and Q is a quinazolinyl radical, the 1-, 2-, 3- or 4-position of which is connected with the alkylene side chain, said quinazolinyl radical bearing in one or both of its 2- and 4-positions a oxo or thioxo group, wherein the benzene ring of said quinazolinyl radical is optionally substituted with 1 to 3 substituents each independently selected from the group consisting of halo, lower alkyl, lower alkyloxy, trifluoromethyl, nitro and cyano, and wherein the pyrimidino ring of said quinazolinyl radical may be partly or fully saturated, said pyrimidino ring being optionally substituted with 1 to 3 substituents independently selected from the group consisting of lower alkyl, aryl, aryl(lower alkyl), thienyl, pyridinyl, thienyl (loweralkyl), and pyridinyl (loweralkyl);

wherein said aryl as used in the definition of said Ar and of said Q is a member selected from the group consisting of phenyl substituted with from 1 to 2 substituents each independently selected from the group consisting of halo, lower alkyl, lower alkyloxy, trifluoromethyl and amino.

7. An anti-congestive composition according to claim 6 wherein X is CO.

8. An anti-congestive composition according to claim 7 wherein Alk is an 1,2-ethanediyl radical.

9. An anti-congestive composition comprising an inert carrier and as an active ingredient an effective anti-congestive amount of a chemical compound selected from the group consisting of 3-[2-[4-(4-fluorobenzoyl)-1-piperidinyl]ethyl]-2,4(1H,3H)-quinazolinedione and the pharmaceutically acceptable acid-addition salts thereof.

10. An anticongestive composition according to claim 6 wherein Ar is an arly radical, X is >C=O, Alk is an alkylene chain having 2 or 3 carbon atoms; and Q is connected to the alkylene side chain by the 2- or 3-position.

11. A method of treating congestion in warm-blooded animals which comprises the administration thereto of an effective anticongestive amount of a chemical compound selected from the group consisting of a quinazoline compound having the formula

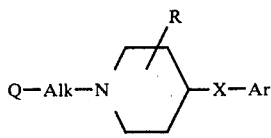

and the pharmaceutically acceptable acid addition salts thereof, wherein:

Ar is a member selected from the group consisting of aryl, thienyl, and pyridinyl radicals;

X is a member selected from the group consisting of

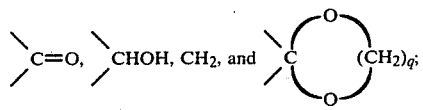

wherein said q is the integer 2 or 3;

R is a member selected from the group consisting of hydrogen, hydroxy and lower alkyl;

Alk is an alkylene chain having from 1 to 4 carbon atoms; and

Q is a quinazolinyl radical, the 1-, 2-, 3- or 4-position of which is connected with the alkylene side chain, said quinazolinyl radical bearing in one or both of its 2- and 4-positions a oxo or thioxo group, wherein the benzene ring of said quinazolinyl radical is optionally substituted with 1 to 3 substituents each independently selected from the group consisting of halo, lower alkyl, lower alkyloxy, trifluoromethyl, nitro and cyano, and wherein the pyrimidino ring of said quinazolinyl radical may be partyly or fully saturated, said pyrimidino ring being optionally substituted with 1 to 3 substituents independently selected from the group consisting of lower alkyl, aryl, aryl(loweralkyl), thienyl, pyridinyl, thienyl (loweralkyl), and pyridinyl (lower alkyl);

wherein aryl as used in the definition of said Ar and of said Q is a member selected from the group consisting of penyl and phenyl substituted with from 1 to 2 substituents each independently selected from the group consisting of halo, lower alkyl, lower alkyloxy, trifluoromethyl and amino.

12. A method according to claim 11 wherein X is CO.

13. A method according to claim 12 wherein Alk is an 1,2-ethanediyl radical.

14. A method of treating congestion in warm-blooded animals which comprises the administration thereto of an effective anti-congestive amount of a chemical compound selected from the group consisting of 3-[2-[4-(4-fluorobenzoyl)-1-piperidinyl]ethyl]-2,4(1H, 3H)-quinazolinedione and the pharmaceutically acceptable acid addition salts thereof.

15. A method according to claim 11 wherein Ar is an aryl radical, X is >C=O, Alk is an alkylene chain having 2 or 3 carbon atoms; and Q is connected to the alkylene said chain by the 2- or 3-position.

* * * * *